US 9,456,874 B2

(12) United States Patent
Kubiak et al.

(10) Patent No.: US 9,456,874 B2
(45) Date of Patent: *Oct. 4, 2016

(54) GRID PATTERNED ALIGNMENT PLATE FOR IMAGING APPARATUS AND METHOD OF PROVIDING IMPLANT PLACEMENT

(71) Applicant: ORTHOGRID SYSTEMS, INC., East Salt Lake City, UT (US)

(72) Inventors: Erik Noble Kubiak, Salt Lake City, UT (US); Jeremy Gililland, Salt Lake City, UT (US); Richard Boddington, Austin, TX (US); Edouard Saget, Boise, ID (US); Steven Samuel Louis, Hinsdale, IL (US)

(73) Assignee: OrthoGrid Systems, Inc, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/431,320

(22) PCT Filed: Feb. 18, 2014

(86) PCT No.: PCT/US2014/016891
§ 371 (c)(1),
(2) Date: Mar. 26, 2015

(87) PCT Pub. No.: WO2014/127354
PCT Pub. Date: Aug. 21, 2014

(65) Prior Publication Data
US 2015/0272695 A1    Oct. 1, 2015

Related U.S. Application Data

(60) Provisional application No. 61/765,940, filed on Feb. 18, 2013.

(51) Int. Cl.
*A61B 19/00* (2006.01)
*A61B 6/00* (2006.01)
*A61B 6/12* (2006.01)

(52) U.S. Cl.
CPC ............ *A61B 19/5225* (2013.01); *A61B 6/12* (2013.01); *A61B 6/485* (2013.01); *A61B 6/487* (2013.01); *A61B 6/505* (2013.01); *A61B 6/5217* (2013.01); *A61B 6/5229* (2013.01); *A61B 6/5294* (2013.01)

(58) Field of Classification Search
CPC ..................................... A61B 6/507
See application file for complete search history.

(56) References Cited

U.S. PATENT DOCUMENTS 5,105,457 A    4/1992 Glassman
6,366,796 B1   4/2002 Yanof et al.
(Continued)

OTHER PUBLICATIONS

U.S. Appl. No. 14/181,887, Kubiak, et al.
(Continued)

*Primary Examiner* — Serkan Akar
(74) *Attorney, Agent, or Firm* — Harris, Shelton, Hanover & Walsh; Susan B. Fentress

(57) ABSTRACT

A computer implemented system for adjusting the placement of an implant in a patient through the use of a dimensioned grid template placed relative to patient anatomy on a fluoroscopic machine and a method to digitally quantify alignment parameters is provided. This system can be used for determining: 1) leg length, offset, and cup position during arthroplasty replacement surgery; 2) fracture reduction/correction position during trauma procedures and 3) an apparatus to be used for deformity correction planning is provided; 4) placement and positioning of instruments and implants relative to bone and anatomical architecture; 5) bone anatomy boundary parameter identification relative to reaming and cutting landmarks of bone.

6 Claims, 35 Drawing Sheets

(56) References Cited

U.S. PATENT DOCUMENTS

| | | |
|---|---|---|
| 7,853,311 B1 | 12/2010 | Webb |
| 8,041,089 B2 | 10/2011 | Drumm et al. |
| D664,661 S | 7/2012 | Kubiak et al. |
| 8,403,967 B2 | 3/2013 | Orbay |
| 8,611,504 B2 | 12/2013 | Kubiak et al. |
| 8,831,324 B2 | 9/2014 | Penenberg |
| 2005/0059873 A1 | 3/2005 | Glozman et al. |
| 2009/0306679 A1 | 12/2009 | Murphy |
| 2010/0086185 A1 | 4/2010 | Weiss |
| 2011/0191084 A1 | 8/2011 | Cooke |
| 2012/0207359 A1 | 8/2012 | Konukoglu |
| 2012/0310097 A1 | 12/2012 | Whitman et al. |
| 2014/0128717 A1 | 5/2014 | Lytle |

OTHER PUBLICATIONS

U.S. Appl. No. 14/692,863, Kubiak, et al.

| LEG LENGTH / OFFSET | SHORT | GOOD | LONG |
|---|---|---|---|
| MEDIAL | 1- ADD HEAD LENGTH<br>2- UPSIZE STEM | 1- LATERAL OFFSET (if pure lateral)<br>2 - ADD HEAD LENGTH (if Coxa vara stem) | 1- REDUCE HEAD LENGTH<br>2- LATERAL OFFSET<br>3- ADD CALCAR CUT |
| GOOD | 1 - UPSIZE STEM | GOOD | 1- ADD CALCAR CUT |
| LATERAL | 1- UPSIZE STEM<br>2- REDUCE HEAD LENGTH<br>3- REDUCE ACETABULAR OFFSET (Liner or ream) | 1- REDUCE ACETABULAR OFFSET (Liner or Ream) | 1- REDUCE HEAD LENGTH<br>2- REDUCE ACETABULAR OFFSET<br>3- ADD CALCAR CUT |

FIG. 13

(1) Original Standing Pelvis X-ray
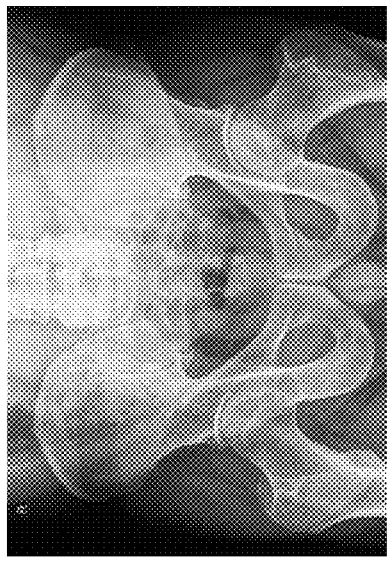
(2) 1st Intraop image
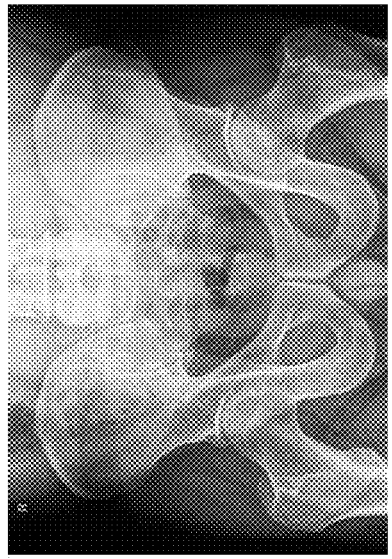
(3) 2nd Intraop image
(4) 3rd Intraop image
FIG. 27A

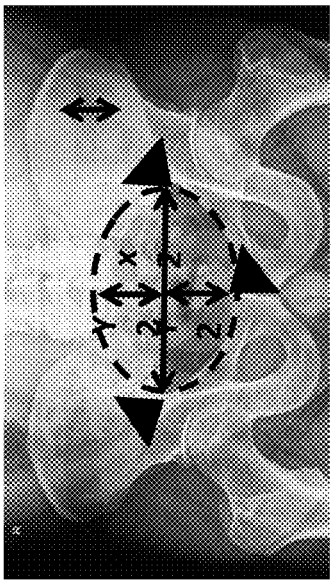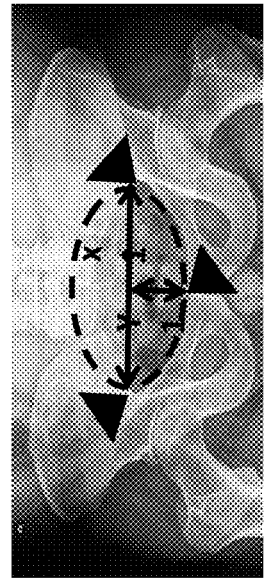
FIG. 27B

GRID PATTERNED ALIGNMENT PLATE FOR IMAGING APPARATUS AND METHOD OF PROVIDING IMPLANT PLACEMENT

CROSS REFERENCE TO RELATED APPLICATIONS

This application is a §371 National Stage Application of PCT/US14/16891 application filed Feb. 18, 2014 and U.S. provisional patent application Ser. No. 61/765,940 filed Feb. 18, 2013, under 35 U.S.C. §111(a) (hereby specifically incorporated herein by reference).

STATEMENT REGARDING FEDERALLY SPONSORED RESEARCH OR DEVELOPMENT

None.

REFERENCE TO SEQUENCE LISTING, A TABLE FOR A COMPUTER PROGRAM LISTING, COMPACT DISC APPENDIX

None.

The present invention relates to a computer implemented system for positioning and adjusting the placement of an implant or instruments or bone fragment or reconstruction of anatomical bone architecture in a patient through the use of a dimensioned radio-opaque pre-dimensioned template placed relative to a patient's anatomy visible intraoperatively via the use of a fluoroscopic machine and a method to digitally quantify the alignment and placement parameters in any and all musculoskeletal applications such as joint arthroplasty, and trauma.

This system includes means for capturing x-ray images in a computer, applying software algorithmic processing to calibrate images, anatomically match images, recognize patterns of images relative to each other, measure anatomical bone/implant differences, and align and position and quantify placement of implant or instrument or bone.

BACKGROUND OF THE INVENTION

Many of the radiographic parameters essential to total hip arthroplasty (THA) component performance, such as wear, and stability, can be assessed intraoperatively with fluoroscopy. However even with intraoperative fluoroscopic guidance, the placement of an implant or the reduction of a bone fragment may still not be as close as desired by the surgeon. For example, mal-positioning of the acetabular component during hip arthroplasty can lead to problems. For the acetabular implant to be inserted in the proper position relative to the pelvis during hip arthroplasty requires that the surgeon know the position of the patient's pelvis during surgery. Unfortunately, the position of the patient's pelvis varies widely during surgery and from patient to patient. During trauma surgery, proper fracture management, especially in the case of an intra articular fracture, requires a surgeon to reduce the bone fragment optimally with respect to the original anatomy in order to: provide the anatomical with joint the best chance to rehabilitate properly; minimize further long term damage and, if possible, to regain its normal function. Unfortunately, in a fracture scenario, the original anatomical position of these bone fragments has been compromised and their natural relationship with the correct anatomy is uncertain and requires the surgeon to use his/her best judgment in order to promote a successful repair and subsequent positive outcome.

Various devices have been suggested to reduce mal-positioning of these surgical components. For example, a transverse acetabular ligament has been suggested as a qualitative marker of the orientation of the acetabulum. (Archbold H A, et al. The Transverse Acetabular Ligament; an Aid to Orientation of the Acetabular Component During Primary Total Hip Replacement: a Preliminary Study of 1000 Cases Investigating Postoperative Stability, J Bone Joint Surg BR. 2006 July; 88(7):883-7). However, it has been suggested that the acetabulum may be deteriorated due to arthritis. Others have proposed using a tripod device that uses the anatomy of the ipsilateral hemi pelvis as the guide to position the prosthetic acetabular component. U.S. Patent Publication Number 20090306679. This instrument has three points. The first leg is positioned in the area of the posterior inferior acetabulum, a second leg is positioned in the area of the anterior superior iliac spine and a third leg is positioned on the ileum of the subject. U.S. Patent Publication Number 20090306679. Regarding fracture fixation, or a correction of a deformity or malunion, various devices have also been suggested to support proper reconstruction or reduction of bone fragments. For example, a distal radius volar fixation plate has been suggested to act as an invasive, intraoperative quantitative supporting buttress to fix and provide a reference to the surgeon in order to help realign the broken bony anatomy. U.S. Pat. No. 8,403,967 B2. However, a need exists in the industry for a device that is not implantable or invasive and is adaptable to a variety of applications.

SUMMARY OF THE INVENTION

In the light of the foregoing background, it is an object of the present invention to provide a computer implemented system and method for determining and measuring leg length, offset, and cup position during arthroplasty surgery in conjunction with x-ray to measure variables, such as, hip implant position to determine the relative leg length and offset measurements for the implant. Arthroplasty surgery includes, for example: hip (anterior approach), hip (posterior approach), knee, ankle, elbow, and shoulder. Trauma surgery includes any and all musculoskeletal repair in both adult and pediatric patients.

Accordingly, the present invention, in one aspect, is a computer implemented system that digitally quantifies alignment and placement parameters in musculoskeletal applications. It includes a computer system that is coupled to a radioactive beam emitter and a fluorescent detector, wherein the fluorescent detector is aligned to the radioactive beam emitter to capture an image of a patient. The computer system further includes an image capturing module, a calibration and anatomical matching module, and a differential mapping module. The image capturing module is configured to capture an operative image of a portion of the patient's body and also to obtain a reference image of a contra lateral side of that portion of the patient's body. The calibration and anatomical matching module is coupled to the image capturing module and is configured to (a) calibrate the reference image and the operative image to same magnification, (b) identify at least one first anatomic marker in the reference image and at least one second corresponding anatomic marker in the operative image, and (c) produce an overlaid image by overlapping the reference image and the operative image together and anatomically aligning the at least one second anatomic marker against the at least one first anatomic marker on the overlaid image. The differential mapping module is coupled to the calibration and anatomical matching module and is configured to digitally quantify alignment and placement parameters in musculoskeletal applications based on the reference image and the operative image taken by the image capturing module.

In one embodiment, the system further includes a grid pattern that is aligned with the at least one second corresponding anatomic marker in the operative image. In a further embodiment, the grid pattern is a radiolucent dimensioned grid plate with a predefined grid pattern, and the radiolucent dimensioned grid plate is positioned between the patient and said fluoroscopic detector. The differential mapping module utilizes the grid pattern to determine at least one measurement and measures the distance from any key anatomical landmark to any grid line.

In another embodiment, the radiolucent dimensioned grid plate is made of a top surface and a bottom surface. At least one of the top and bottom surfaces has a plurality of dimensioned radio-opaque horizontal and vertical lines. The horizontal and vertical lines are spaced apart with identical distance between each subsequent vertical line in a horizontal direction and each subsequent horizontal line in a vertical direction. The radiolucent dimensioned grid plate further includes an oblique grid line at an angle of between about 30 to 50 degrees relative to the horizontal lines, and a medial-lateral slot formed in one of the top and bottom surfaces of the grid plate to be parallel to the horizontal lines.

In one embodiment, the computer system further includes a microprocessor and a non-transitory computer-readable storage medium coupled to the microprocessor, wherein the non-transitory computer-readable storage medium is encoded with computer-readable instructions that implement functionalities of the modules mentioned above so that when the computer-readable instructions are executed, the microprocessor performs the respective functions accordingly.

In a further embodiment, the computer system further includes an outcome solutions module that is coupled to the differential mapping module. This module presents at least one measurement of surgical variables to the surgeon.

In one embodiment, the outcome solutions module further includes a database which stores a plurality of surgical procedures with each of the procedure catering for a particular operation. During a particular surgical operation, the computer system retrieves a particular surgical procedure from the database and suggests surgical recommendation to the surgeon.

In yet another embodiment, the database stores a plurality of musculoskeletal surgical procedures including hip replacement, knee replacement, shoulder replacement, ankle replacement and elbow replacement; and a plurality of trauma related fracture reduction surgical procedures.

In one embodiment, the surgical variable involves an implant and at least one measurement of surgical variables based on the reference image and the operative image taken by the image capturing module, which facilitates the placement of the implant in the patient based on at least one measurement.

In another aspect, the present invention is a method of adjusting the placement of an implant in a patient. The method includes the following steps: It first captures an operative image of a portion of the patient's body where the implant is to be operated on by a fluorescent detector; and obtains a reference image of a contra lateral side of the corresponding portion of the patient's body. It then identifies at least one first anatomic marker in the reference image and at least one second corresponding anatomic marker in the operative image. An overlaid image is then produced by first overlapping the reference image and the operative image together and then anatomically aligning the at least one second anatomic marker against the at least one first anatomic marker on the overlaid image. Subsequently, the method determines at least one measurement that is vital to the operation of this implant based on the overlaid image so that a surgeon can adjust the placement of the implant in the patient based on said at least one measurement.

In one embodiment, the method further includes a step of calibrating the reference image and the operative image to same magnification using the at least one reference markers.

In one embodiment, the reference image and the operative image are x-ray images and the method employs a variety of image processing and pattern recognition techniques for identifying the anatomic markers. In a further embodiment, a plurality of specialized pattern recognizers are employed for recognizing said anatomic markers with each specialized pattern recognizer specifically designed for recognizing one anatomic markers.

In one embodiment, the measurement quantifies the difference between an anatomic part in the operative image against a corresponding anatomic part in the reference image. In a further embodiment, this is performed using a grid pattern.

In one embodiment, the grid pattern is a software generated virtual grid that is aligned with the at least one anatomic marker in the operative image; and the quantifying step calculates a relative distance between the anatomic part in the operative image and the corresponding anatomic part in said reference image.

In an alternative embodiment, the grid pattern is provided by a radiolucent dimensioned grid plate. The grid plate is positioned in between the patient and the fluorescent detector when both the reference image and the operative image are being acquired so that a reference grid pattern appears on the reference image and an operative grid pattern appears on the operative image. This method then (a) calculates at least one displacement between the reference grid pattern and the operative grid pattern, (b) references the anatomic part in the operative image by the operative grid pattern to produce an operative grid coordinate for the anatomic part; and references the corresponding anatomic part in the reference image by the reference grid pattern to produce a reference grid coordinate, (c) subtracts the operative grid coordinate from the reference grid coordinate and (d) quantifies the measurement by adjusting the subtraction with the displacement.

In another embodiment, the method further generates a report that incorporates the at least one measurement for surgical planning. In a further alternative embodiment, the method further provides the at least one measurement continuously to the surgeon during the whole operation so that the surgeon can adjust the placement of the implant in the patient based on the at least one measurement.

In a specific embodiment, the operation is total hip arthroplasty and the at least one measurement vital to the operation includes leg length difference, offset difference and hip position difference between the operative image and said contra lateral image; or any combination thereof. In a further embodiment, the method further uses a hip variance algorithm for recommending surgical procedure.

In one embodiment, a computer-implemented system for adjusting the placement of an implant in a patient is provided. This system includes: a processor configured to encode images of a patient with respect to a radiolucent dimensioned grid having a plurality of dimensioned radio-opaque horizontal and vertical lines and a grid line at an angle of between about 30 to 50 degrees; compute differential for offset, leg length and cup angle from the images; compute changes in implant position; and present feedback for adjusting the placement of an implant in a patient.

In another embodiment, a computer implemented method using memory and processor is provided. The method includes the steps of: displaying images on a screen; receiving images of a patient with respect to a radiolucent dimensioned grid plate having a plurality of dimensioned radiopaque horizontal and vertical lines and a grid line at an angle of between about 30 to 50 degrees, and a medial-lateral slot in said grid plate; encoding overlap of an operative side and a post operative over mirrored contralateral using the grid; computing changes in implant position and providing feedback for adjusting the placement of an implant in a patient.

In another embodiment, this method includes the steps of obtaining subject specific data from an image of the patient, wherein the data consists of a "Y" axis corresponding to an anatomical axis of the subject and a "X" axis corresponding to an angle related to an abnormality.

There are many advantages of this invention. The system can operate either in a pre-operative mode, where it offers a report to the surgeon for surgical planning purpose, or in an intra-operative mode, where it will continuously calculate the differences of vital measurements between the operative image and the contra lateral image. As such, this invention provides real-time, continuous feedback to the surgeon on how much he needs to correct the implant placement and alignment. Furthermore, this invention can use either a physical dimensioned grid plate, or a software generated virtual grid plate as a guide in determining the measurements.

BRIEF DESCRIPTION OF THE SEVERAL VIEWS OF THE DRAWING

The drawing shows schematically a fluoroscopic alignment plate apparatus and method of use according to an example form of the present invention. The invention description refers to the accompanying drawings:

FIG. 13 is a block diagram of the Hip Variance Algorithm the present invention.

FIG. 27A shows a series of x-ray images of a pelvis wherein an original standing Anterior Posterior (AP) Pelvis x-ray saved within the software pre-operatively is used as an overlay reference intra-operatively so that the surgeon can properly identify the natural standing position of the pelvis prior to commencement of the implantation process. Each intraoperative image is automatically overlaid over the original image until a matching anatomical view is reached and deemed acceptable by the surgeon to proceed.

FIG. 27B illustrates another process by which the application can establish the proper intraoperative determination of a patient's standing pelvic tilt using the inlet measurement as applied to intraoperative x-ray images.

DESCRIPTION OF THE INVENTION

The present invention may be understood more readily by reference to the following detailed description of the invention. It is to be understood that this invention is not limited to the specific devices, methods, conditions or parameters described herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

These and other aspects, features and advantages of the invention will be understood with reference to the detailed description herein, and will be realized by means of the various elements and combinations particularly pointed out in the appended claims. It is to be understood that both the foregoing general description and the following detailed description of the invention are exemplary and explanatory of preferred embodiments of the inventions, and are not restrictive of the invention as claimed. Unless defined otherwise, all technical and scientific terms used herein have the same meaning as commonly understood by one of ordinary skill in the art to which this invention belongs.

DETAILED DESCRIPTION OF THE INVENTION

Figure 1:
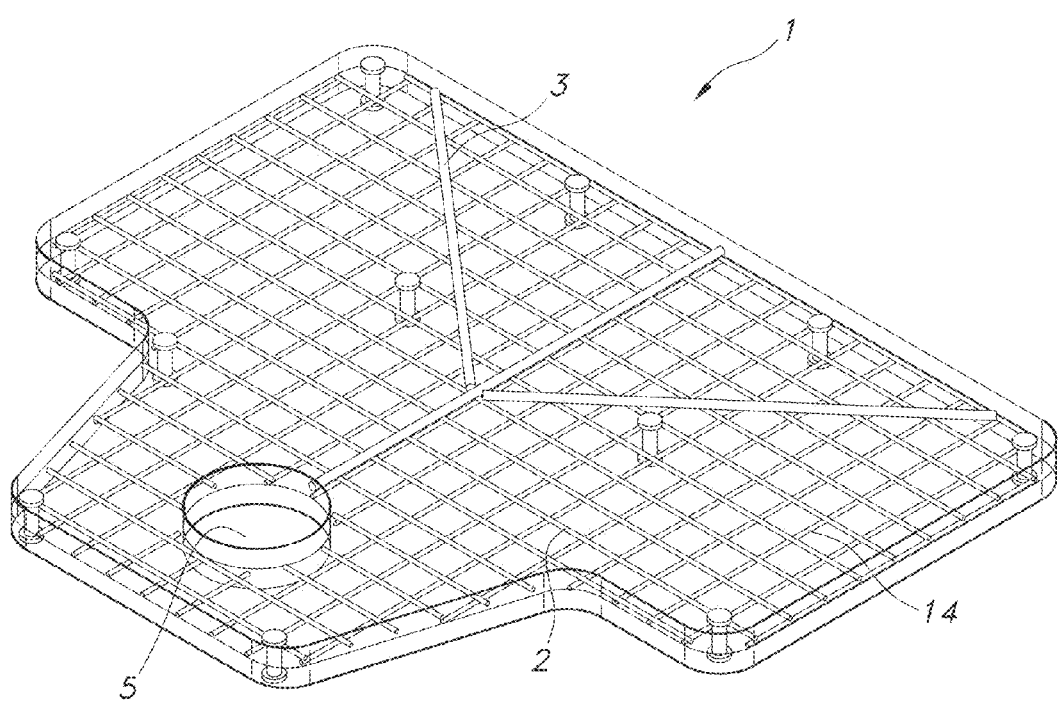
FIG. 1 is a perspective view of an embodiment of the dimensioned grid plate of the present invention.

Now referring to FIG. 1 a radiolucent dimensioned grid plate 1 is designed to be sufficiently large to ensure that the body part in questions, such as the entire pelvis and proximal femurs (left and right), is captured in a fluoro image. The radio-opaque grid (any and all metals, ceramics) has a (1 cm) quantifiable pattern (other quantifiable patterns, English) with each individual "block" having a square geometry. These grid lines align parallel to each other in two directions—vertical (cephalad/caudad) 14 and horizontal (medial/lateral) 2.

Figure 2:
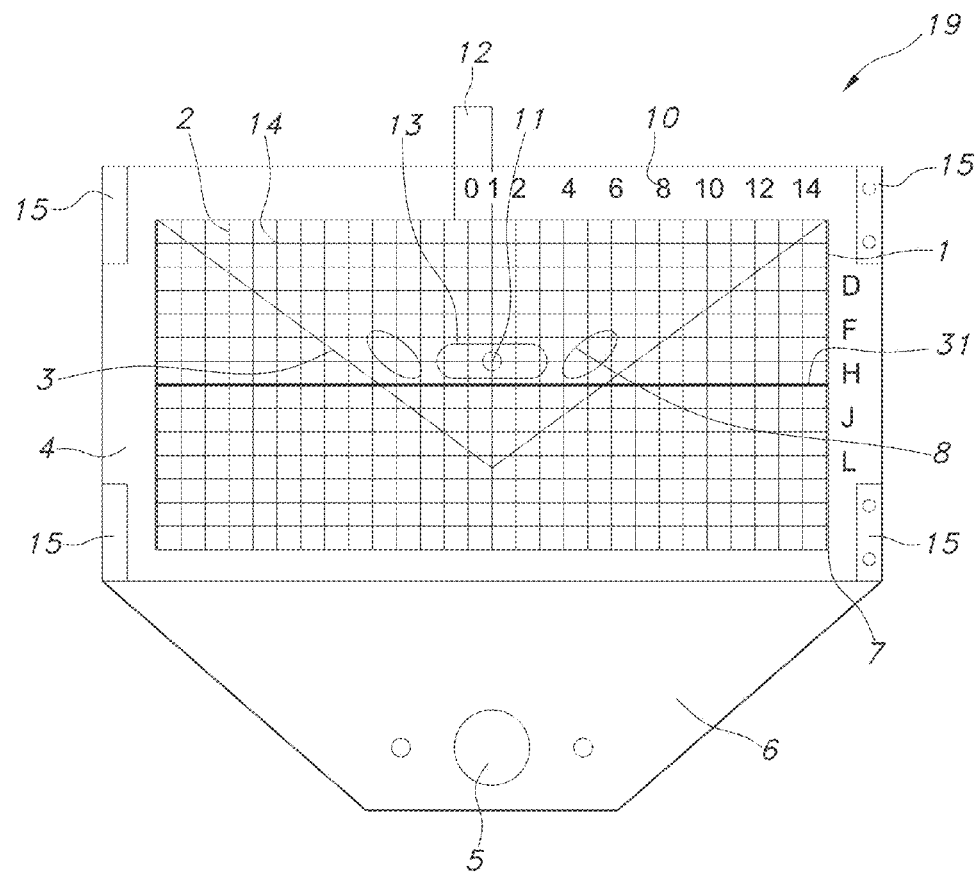
FIG. 2 is a front view of an embodiment of the dimensioned grid plate apparatus of the present invention.

Now referring to FIG. 2, a radiolucent dimensioned grid plate 1 for hip arthroplasty is provided. The dimensioned grid plate 1 is "sandwiched" between support plates 4 that have an extended aspect 6 in the caudal direction, to form the grid plate apparatus 19. This caudal aspect has a cutout 5 that matches and mates with an operating table's peg for use in an anterior approach procedure. The outer layer of the support plates 4 are joined together at the corners 15 by a solid metal piece that will also serve as the attachment place for the clamps that will attach the a dimensioned grid plate apparatus 19 to the operating table 72 or to the hip positioning apparatus (not shown). For strength, support rods (not shown) can be added to the caudal aspect.

In this dimensioned grid plate 1, two grid lines form a V and are angled at 45 degrees to the vertical and horizontal. In this dimensioned grid plate 1, these two lines represent a guide 3 for quantifying the abduction angle of an acetabular cup used during an arthroplasty procedure. However, the desired angle for the guide 3 relates to the type of implant. Metal on metal implants use a 40 degree angle of abduction, while polyethylene based articular surfaces use a 45 degree angle. The left half side of the grid plate apparatus 19 is a mirror image of the right hand side. The dimensioned grid plate 1 can have the following radio opaque markings (any and all methods of etching or marking): Two 45 degree angled radio opaque guide lines 3; two elliptical etchings which represent the proper version of the acetabular component 8 adjacent and cephalad to the 45 degree lines with a distance of approximately 20 cm from the apex of the two 45 lines (correlates to average standardized measurements of human pelvis between the radiolucent lines representing the quadrilateral surface, the roof of the obturator foramen, and the fossa acetabulae (the "teardrop")); numbers representing the vertical lines with zero being the midline and the numbers counted off in both medial and lateral directions from zero 10; letters of the alphabet on both sides of the grid representing the horizontal (x-axis) 9; and an image of an anatomical feature, such as a pelvis outline. All these grid lines and markings guide the physician in defining the orientation for insertion of the implants and specifically determining and measuring leg length, offset, cup placement, and head center of rotation and mechanical axis of lower limb.

The dimensioned grid plate 1 is enclosed on either side in an epoxy resin that is both transparent and with a plurality of support plates 4 to form the grid plate apparatus 19. The epoxy creates a complete seal for the metal to prevent corrosion and support cleanability of the grid plate apparatus 19. Other manufacturing processes known to those skilled in the art include: laser etched: etched, then filled with radio-opaque marker in etched negative areas, then sandwiched; molded: with metal on support plates 4; using tungsten as the radio-opaque material for use in grid lines and numbers; sandwich deposition: printing process (like circuit boards); CNC Machined: back filled and radio-opaque decal: use of radio-opaque ink placed on support plates 4.

Figure 3:
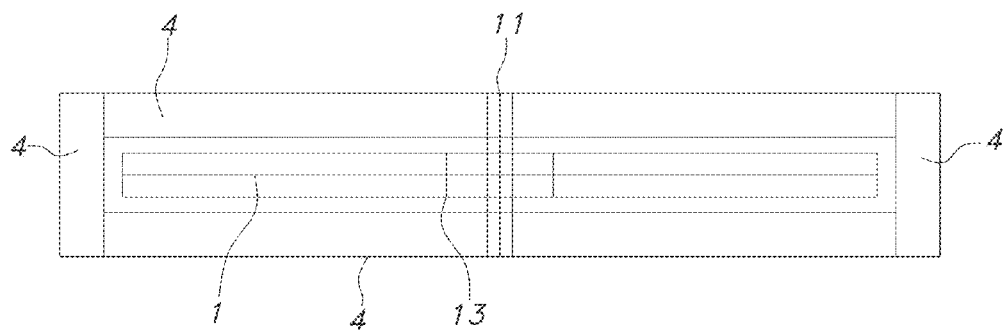
FIG. 3 is a side view of an embodiment of the dimensioned grid plate apparatus of the present invention.

Now referring to FIG. 3, the plurality of support plates 4 is shown surrounding the dimensioned grid plate 1. This central axis pin 11 is attached to the outer support plates 4, by conventional means such as a screw threaded through the support plate into the end of the axis pin 11. The axis pin 11 will be captured on either end by a screw threaded through the support plates 4 and into the end of the axis pin—on both ends. The medial-lateral slot 13 allows +/−5 cm medial-lateral translation of the dimensioned grid plate 1 relative to the support plates 4. The central axis pin 11 is oriented perpendicularly to the surface of the plurality of support plates 4 and the central axis pin 11 projects upwardly. This dimensioned grid plate 1 has a slot 13. The slot 13 allows the dimensioned grid plate 1 to be shifted from side to side or medially-laterally.

Figure 4A:
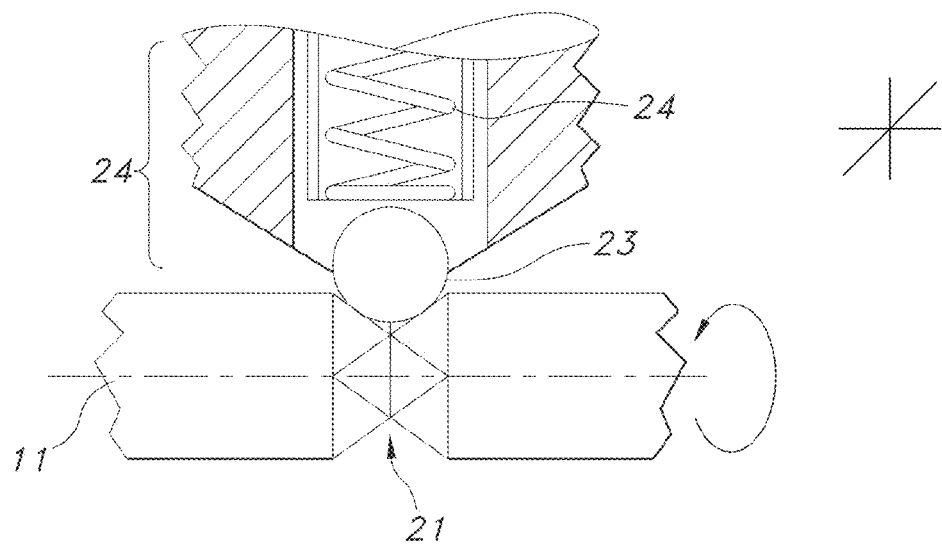
FIG. 4A is a side view of the apparatus of the apparatus of the present invention.
Figure 4B:
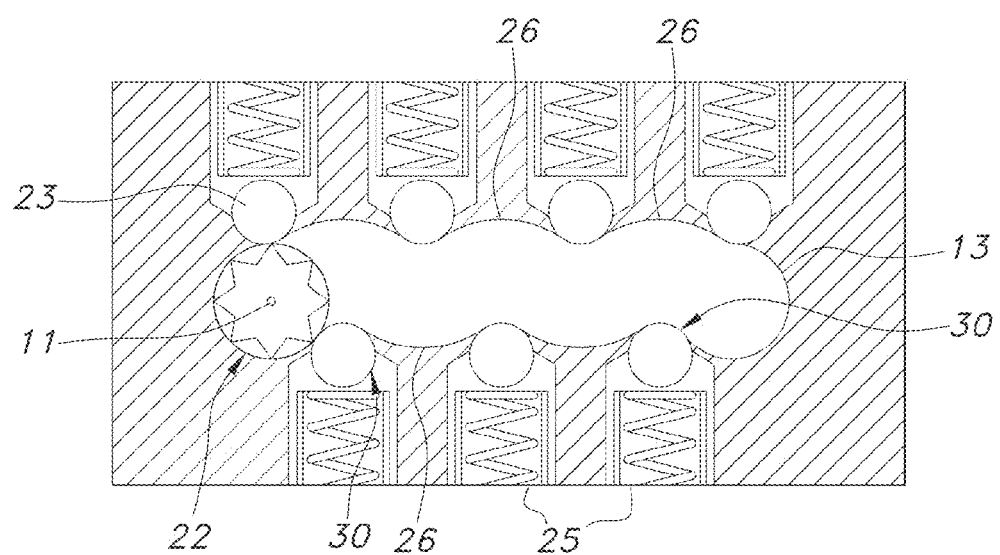
FIG. 4B is a top view of the translational/rotational mechanism of the present invention.

Now referring to FIGS. 4A and 4B, the dimensioned grid plate 1 articulates within the support plates 4 by a central axis pin 11. The medial-lateral slot 13 allows +/−5 cm medial-lateral translation of the dimensioned grid plate 1 relative to the support plates 4 and the patient 27. The dimensioned grid plate 1 can also be rotated +/−40 degrees about the central axis pin 11 axis relative to the support plates 4 and the patient 27. The dimensioned grid plate 1 is rotated or translated by using the handle 12 that is attached to the grid plate apparatus 19. The dimensioned grid plate 1 rotates about the central axis pin 11.

The slot 13 is configured with scalloped sides or edges that allow the dimensioned grid plate 1 to be indexed at a plurality of positions. The central axis pin 11 has a groove 21 about which the dimensioned grid plate 1 will rotate. The central axis pin groove 21 will further have a series of countersunk grooves 22 for engagement of spring-loaded ball 23 (for location of rotational position of the dimensioned grid plate 1 relative to the outer support plates. Furthermore, the dimensioned grid plate 1 translates in a medial lateral direction along the central axis pin 11. This translational movement is achieved by utilizing countersunk grooves 26 with a spring-loaded device (SLD) 24 having a uniform groove and countersunk slot configuration. The indexing is accomplished by a translation/rotational mechanism 25. The central axis pin 11 has the ability to translate along the medial-lateral slot 13 and engage in any one of a series of positions in the medial lateral direction. This is accomplished by having a plurality of spring-loaded device 25 used in conjunction with a plurality of corresponding countersunk slots 26. This rotation is accomplished by the configuration of the medial lateral slot 13.

The slot 13 is made of a plurality countersunk grooves 26 that are configured to retain the central axis pin 11. Additionally, the surface opposite 30 one of the plurality of countersunk grooves 26 is configured to retain a spring-loaded device 24. A plurality of spring-loaded devices 24 mediate the movement of the grid 1. The spring-loaded device 25 releasably holds the central axis pin 11 in the selected scalloped or notched position. The engagement/disengagement position and force will be determined based upon spring-loaded device holding capacity. The central axis pin 11 can be fluted longitudinally 22 which allows a rotational detent action as the patient (on the grid plate apparatus 20) is rotated in the horizontal plane about the central axis pin 1.

Figure 5:
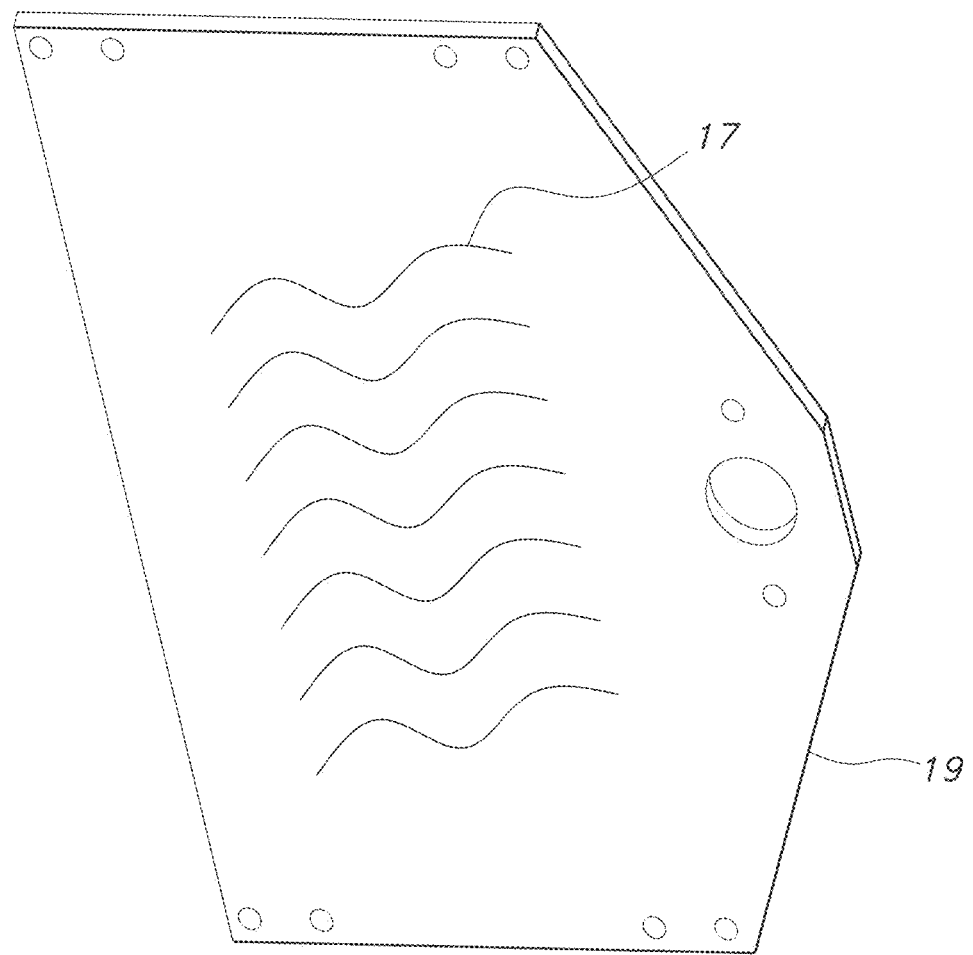
FIG. 5 is a rear view of an embodiment of the dimensioned grid plate apparatus of the present invention.

Now referring to FIG. 5, on the underside of the grid plate apparatus 19 there are strips of an adhesive material such as VELCRO 17 to further secure the plate to the table. This prevents the grid plate apparatus 19 from moving relative to the surgical table or patient during the surgical procedure.

Figure 6A:
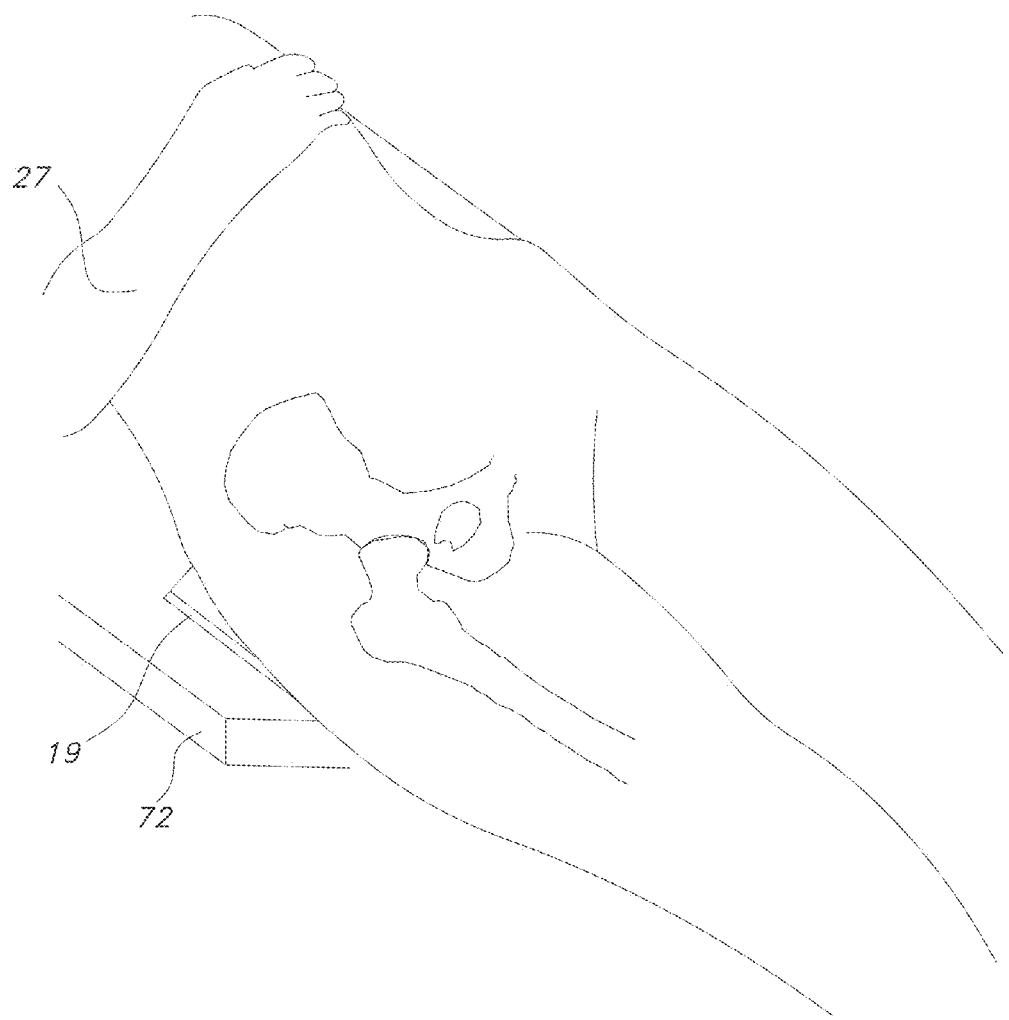
FIG. 6A is an illustrative sketch showing the relationship of the patient to the apparatus in an anterior approach.
Figure 6B:
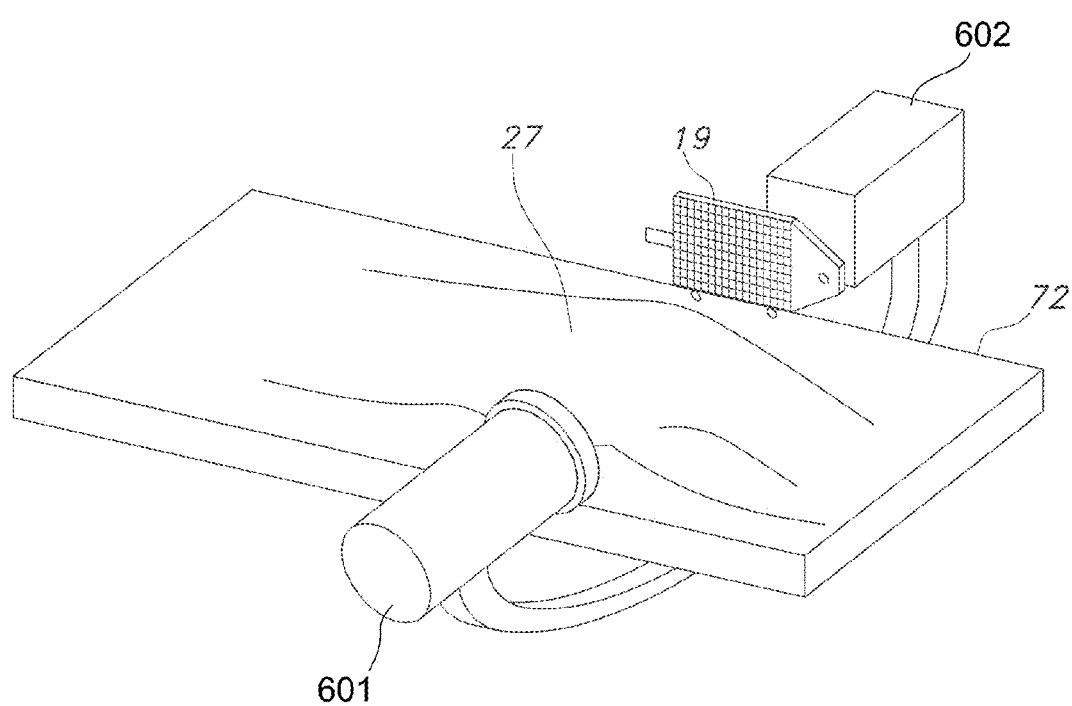
FIG. 6B is an illustrative sketch showing the relationship of the patient to the apparatus in a posterior approach.

Now referring to FIG. 6A, this embodiment allows for use in all surgical approaches to the hip. For the anterior approach, the grid plate apparatus 19 is used as shown in FIG. 6A, the patient is in a supine position with the grid apparatus 19 placed beneath the patient's pelvis. For the posterior approach as shown in FIG. 6B the added benefit is having the ability to rotate, translate ML, and ideally position the grid to the anatomy of the patient. The dimensioned grid plate 1 has the ability to rotate +/−40 degrees from the vertical and translate in the medial lateral direction +/−5 cm. The dimensioned grid plate 1 can translate cephalad/caudad by adjusting the clamps which fix the dimensioned grid plate apparatus 19 to the bed or the hip positioning device. The rotational/translational grid can also be used for an anterior approach procedure. The Hilgenreiner's line 31 is a line drawn horizontally through the superior aspect of both triradiate cartilages. It should be horizontal, but is mainly used as a reference for Perkin's line and measurement of the acetabular angle.

The grid plate apparatus 19 has an extension in the caudad direction that has enough distance to allow the grid to lock onto the operating table 72 and then also ensure that the dimensioned grid plate apparatus 19 is directly behind (posterior) the patients' pelvis. The extension piece has a slot 5 cut out that matches the diameter of the peg (not shown) on the surgical table 72 that is being used. The peg (not shown) is fixed to the table and so by locking the peg to the plate there will be no motion of the plate 19 relative to the patient 27 during the surgery. In testing that was performed, tables that are conducive to the direct anterior approach were used. The present apparatus 1 and method can be used on any radiolucent operating table.

For a posterior surgical approach, FIG. 6B, the patient 27 is placed in the appropriate position for hip replacement surgery. The surgeon places the patient 27 in a Lateral Decubitus position; the surgeon positions the dimensioned grid plate 19 directly behind the pelvis of the patient 27. Once the surgeon has the trial implants or final implants inserted in the correct position inside the body, he or she will bring in the mobile x-ray machine (C-arm) and align the C-arm beam with the pelvis and grid plate in the anterior posterior plane. The image generated by the C-arm will provide a fluoro view of the anterior posterior pelvis and a grid pattern overlay. For the use in a posterior surgical approach, the patient 27 can be placed on his or her side in an appropriate and traditional manner. The surgeon will examine the x-ray image to determine subject specific data. Three parameters will be measured and determined at this point: 1) leg length, 2) offset, and 3) cup position.

Leg length: In quantifying leg length discrepancy, the patient's anatomical landmark(s) can be geometrically dimensioned relative to the grid lines. For example, points on the grid line drawn through the bottom of the ischium may be viewed as points on the grid marked along the H grid line. The proximal aspect of the left and right lesser trochanters may be viewed as points on the grid marked as G3 and F3 respectively.

The distance measured counting or using the grid squares between the ischial axis grid line and the respective two lesser trochanter points (G3 and F3 for example) is the leg length discrepancy. Alternatively, a surgeon's preference may be to use points on the grid marking the greater trochanter in conjunction with the grid lines through the obturator foramina.

Offset. The offset of the component is the distance from the center of rotation of the head to a line bisecting the long axis of the stem.): In a similar technique to leg length, offset can be quantified. Corresponding radiographic points identified on the patient's left and right pelvis and proximal femur can be measured with the grid lines and blocks. The difference between the left and right measurements will quantify the offset mismatch and provide the surgeon with a numerical number to allow restoration of proper offset.

Pelvic Acetabular Implant commonly referred to as the "cup": The optimal position of the acetabular component can be determined using the dimensioned grid plate apparatus 19 as an alignment and measurement device. The dimensioned grid plate apparatus 19 has a 45 degree angled metal line 3. The radiographic image will display the trial or final implanted acetabular cup positioned in the acetabulum relative to the 45 degree guide line 3 that will be superimposed on the image. The cup position can then be adjusted based upon image feedback until correct positioning of the final implant is determined.

Figure 7:
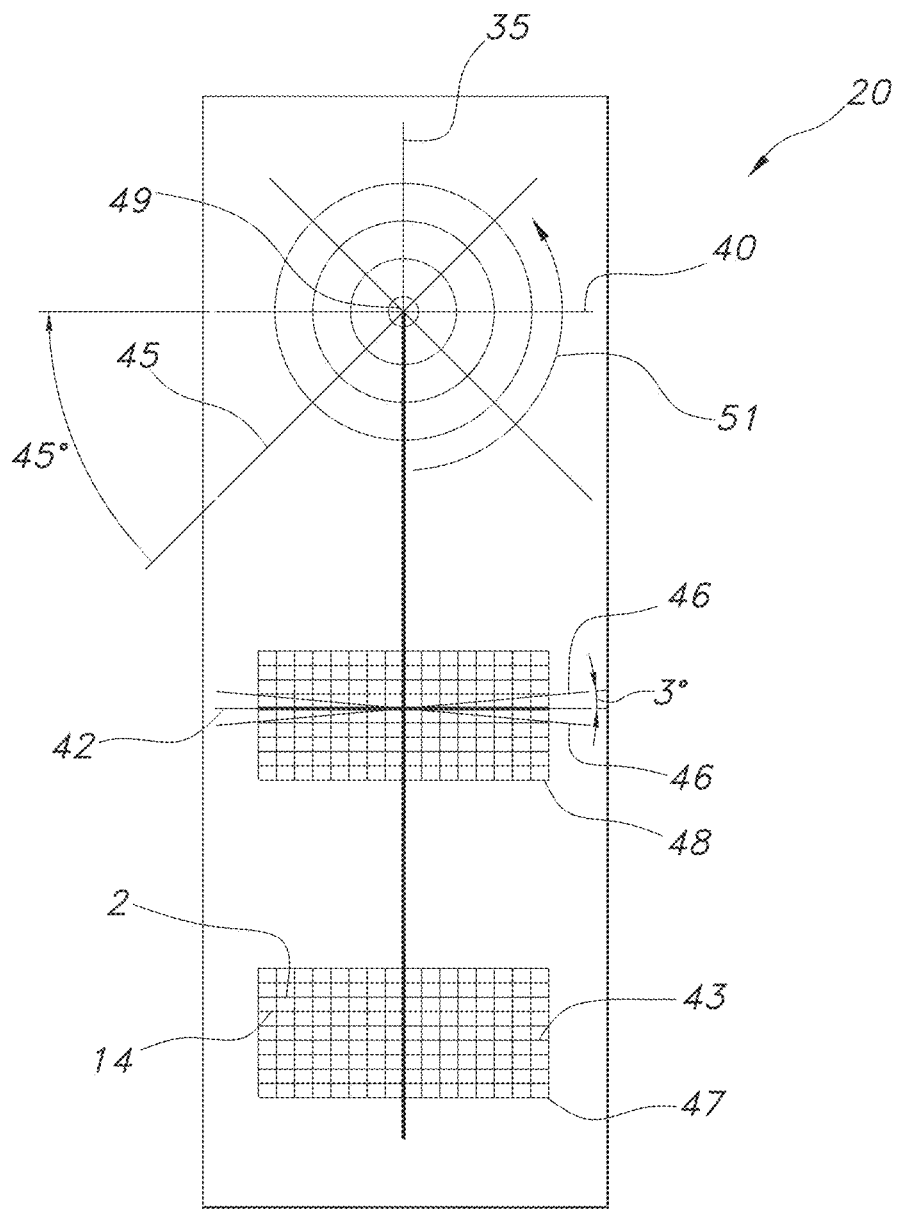
FIG. 7 is a front view of another embodiment of the dimensioned grid plate apparatus of the present invention.
Figure 8:
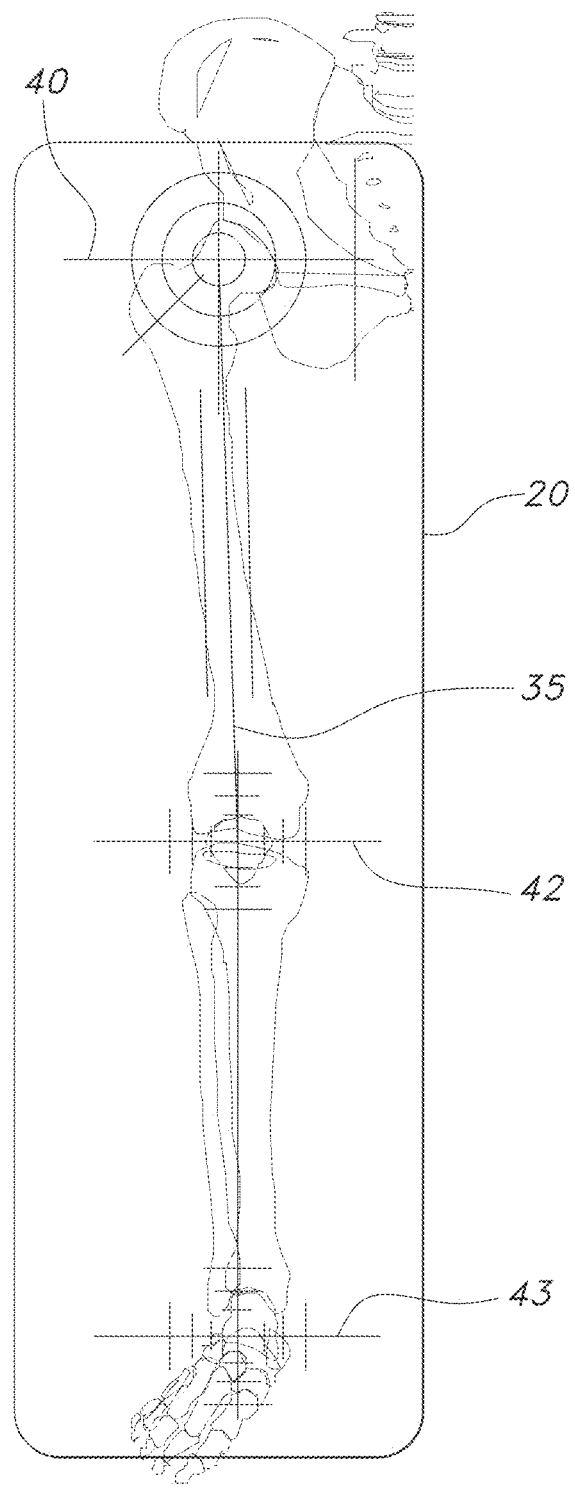
FIG. 8 is a sketch of x-ray view showing hip anatomy with implant and the grid overlay.

Now referring to FIGS. 7-8 a dimensioned grid plate 20 can be adapted for a variety of end-uses such as to facilitate the placement of an implant in arthroplasty or trauma procedure; for fracture reduction/correction during a trauma procedure or for deformity correction planning. In operation, the proximal angle at 40 is determined. Next the distal angle is determined at 42. Next the proximal tibial angle 43 is determined. Next the distal tibial angle 43 is determined to form the "X" axis relative to the "Y" axis 35 of the dimensional grid plate apparatus 20.

The Y axis 35 is the center line that creates a mirror image of grid and reference lines on either side of it, thus allowing use for either a left or a right leg application. 49 marks the center of the head location. The proximal pelvic section of the device also has two 45 degree lines 45 that intersect at the center of the head point 49. These same lines can also be used to quantify neck angle 51. The knee section 48 is made of a grid pattern matching that of grid plate 20. Similarly, the ankle section is made of a grid pattern matching that of grid plate 20. The knee section has a central x-axis 42. Similarly, the ankle section has central x-axis 43. The knee section 48 has two 3 degree lines 46 for use in quantifying alignment as needed.

In another embodiment, and now referring to FIG. 8, a dimensioned grid plate apparatus 20 for use with a trauma procedure on a lower extremity is disclosed. The trauma implications go beyond the pelvis and acetabulum. A larger grid plate 20 that runs from the patient's pelvis to beyond the ankle allows a surgeon to confirm length using the contralateral side. Additionally, the grid plate 20 allows the surgeon to confirm alignment prior to and after placement of an implant. The y-axis 35 correlates with the mechanical axis that runs from the head of the femur through bony landmarks in the tibial plateau through to the distal tibia. Angles that may create the x-axis 40 (depending upon fracture location) could be: proximal angle; lateral distal angle; medial proximal tibial angle; distal tibial angle.

Figure 9:
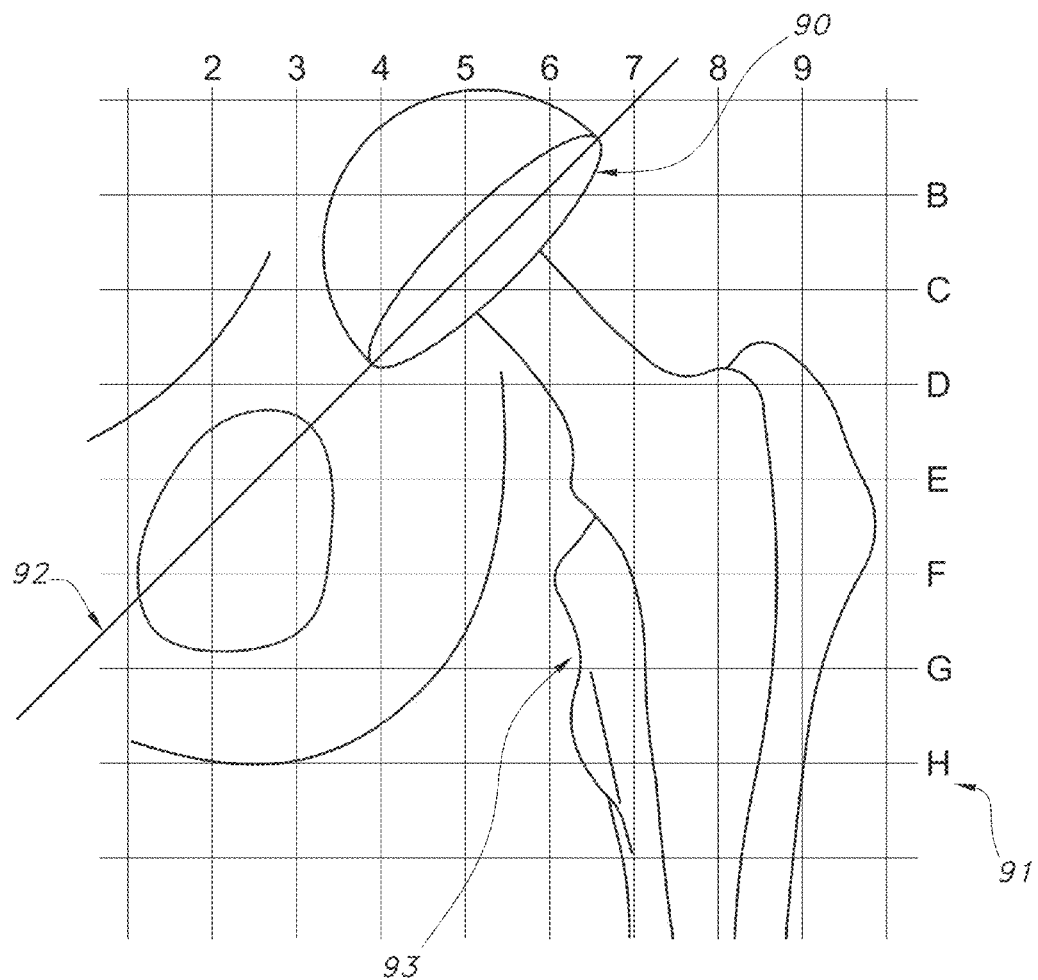
FIG. 9 is a schematic of an x-ray view of the hip anatomy with implant grid overview.

Now referring to FIG. 9, an x-ray view of hip anatomy within implant and grid overview is shown. In quantifying leg length discrepancy, the patient's anatomical landmark(s) can be geometrically dimensioned relative to the grid lines. For example, points on the grid line drawn through the bottom of the ischium may be viewed as points on the grid marked along the H grid line 91. For example the proximal aspect of the left lesser trochanters of the affected hip may be viewed as A point on the grid marked as G6.5 93 on the unaffected hip it can be determined that this same point is G5.5. For example, the distance measured counting or using the grid squares between the ischial axis grid line H 91 and the respective two lesser trochanter points (G6.5 and G5.5 for example) is the leg length discrepancy, relating to the inserted cup 90.

In another embodiment, deformity correction works much the same as the trauma description above. An existing deformity is evaluated against the patient's contralateral side. The grid plate apparatus 19 or 20 is used to ensure that the bone length and alignment correlate to the contralateral side. The grid plate apparatus 19 or 20 allows the surgeon to evaluate whether the osteotomy is sufficient to correct alignment and/or length intraoperatively, as well as making it visually easier to plan a correction procedure by using the grid to obtain pre-operative radiographs (i.e., surgeon does not have to draw his own lines and angles on plain radiographs to try to determine the appropriate amount of bone to remove and/or cut and re-angle).

Figure 19:
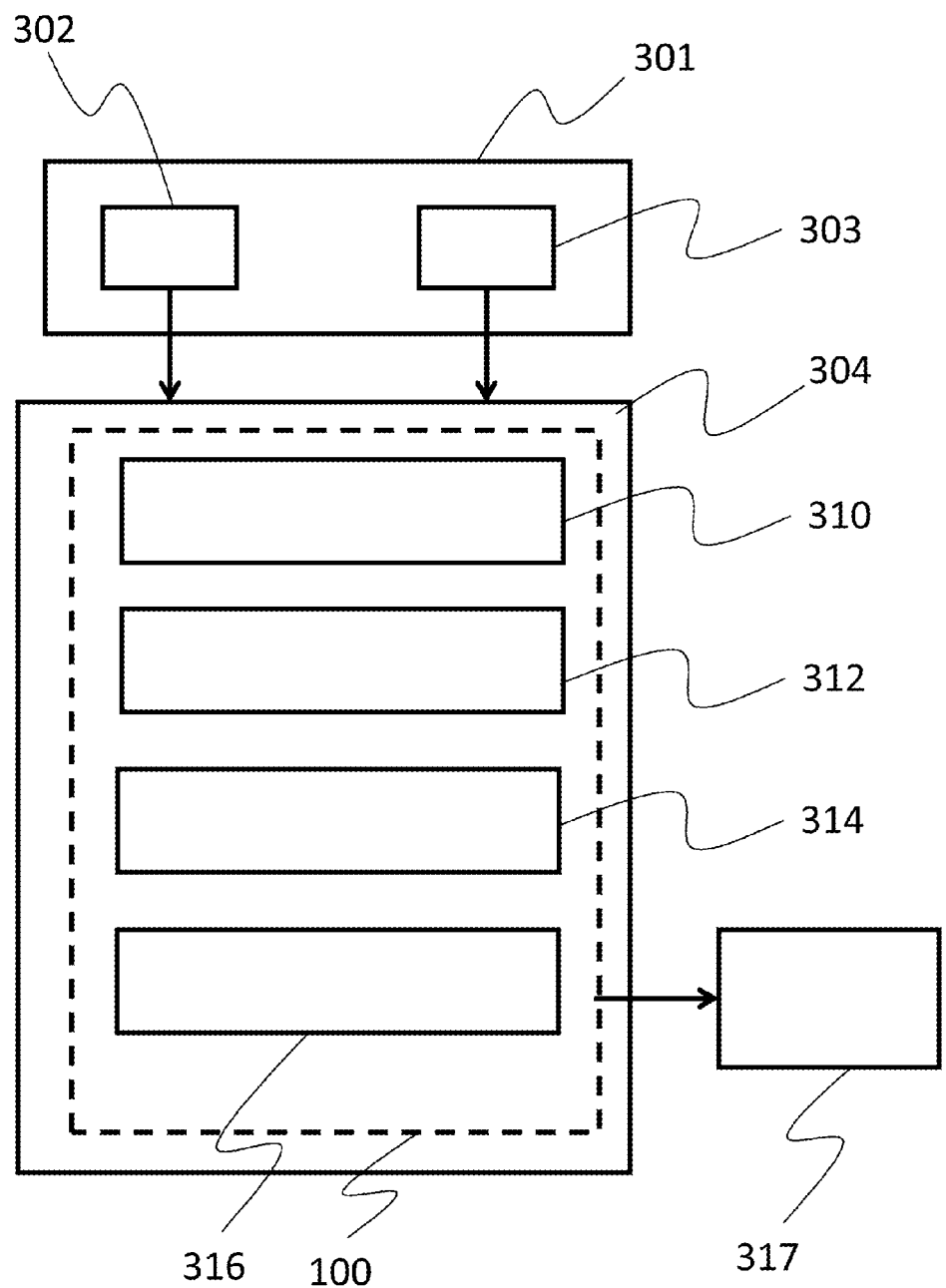
FIG. 19 is a system configuration diagram of the computer-aided surgical operation system in another embodiment of the present invention.

FIG. 19 is an exemplary system configuration of a computer-aided surgical operation system that implements the present invention. It includes fluoroscopic equipment 301 that further incorporates a radioactive ion beam emitter 302 and a fluorescent detector 303 that captures the radioactive ion beam and forms a digital image. In one embodiment, the radioactive ion beam emitter 302 is an x-ray emitter and is mounted at one end of the C-arm while the fluorescent detector 303 is an x-ray detector and is mounted at the opposite side of the C-arm. Both the radioactive ion beam emitter 302 and a fluorescent detector 303 are coupled to a computer 304. The computer 304 includes one or more processors and a non-transitory computer-readable storage medium coupled to the processor. The non-transitory computer-readable storage medium is encoded with computer-readable instructions which form the software system 100. The software system 100 includes an image capturing module 310 that captures and stores the digital image acquired by the fluorescent detector 303. In one embodiment, the image is in the DICOM image format. The acquired image is sent to the calibration and anatomical matching module 312 for analysis. The analysis result is fed to a differential mapping module 314 to determine at least one measurement that is vital to a surgical operation. This module is also configured to digitally quantify alignment and placement parameters in musculoskeletal applications based on the acquired images. The at least one measurement is then sent to an outcome solutions module 316. This module presents the at least one measurement to the surgeon so that the surgeon can make correct implant placement and alignment. The functionalities of these software modules (310 to 316) will be discussed in details below.

In one embodiment, the computer system 304 is coupled to a monitor screen 317 that is configured to display the radiographic images and other relevant text and graphic information to the surgeon. It may also couple to input peripheral devices such as keyboard, mouse, trackball or similar pointing devices (not shown), as well as network communication peripherals (not shown) so that it can communicate with other external servers and computer.

The computer-aided surgical operation system may operate in two modes. In a pre-operative mode, the system is to produce at least one measurement for the surgeon to plan the operation. The surgeon may study the digital x-ray images taken from the patient, comparing them against normal cases, and develop the surgical plan. When the surgeon is performing the operation, the system can operate in intra-operative mode whereby the surgeon can make use of the system as a guide for adjusting the placement of an implant to the patient.

In operation, the patient is placed on the operating table 72 either in the supine position (anterior approach hip) as shown in FIG. 6A or in the lateral position (posterior approach), or any other operative position indicated for surgery (trauma, spine etc) as shown in FIG. 6B. The x-ray emitter 602 is mounted on one side of the C-arm while the x-ray detector 601 is mounted on the opposite site as shown in FIG. 6B. The grid plate apparatus 19 or 20 may or may not be used during the surgical operation.

Figure 10:
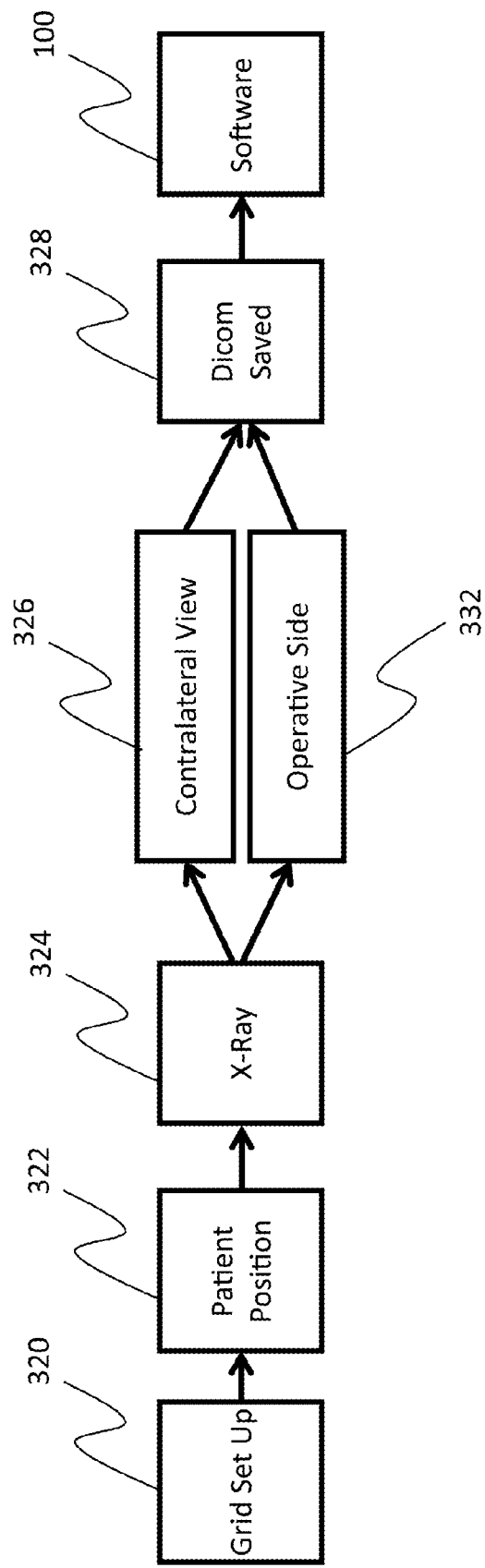
FIG. 10 is a block diagram of the preoperative set up of the present invention.

Now referring to FIG. 10, the pre-operative set up is provided. The grid plate apparatus 19 or 20 is set up as needed in step 320. In the event of utilization of software generated grid then there will be no need to set up grid plate and this step is not necessary. The patient is positioned and. x-ray reference markers are attached to patient or positioning device in step 322. An x-ray is taken of both the contra lateral and operative sides (steps 324, 326 and 332). A DICOM image is saved (step 328) and transmitted to the software system 100.

Figure 11:
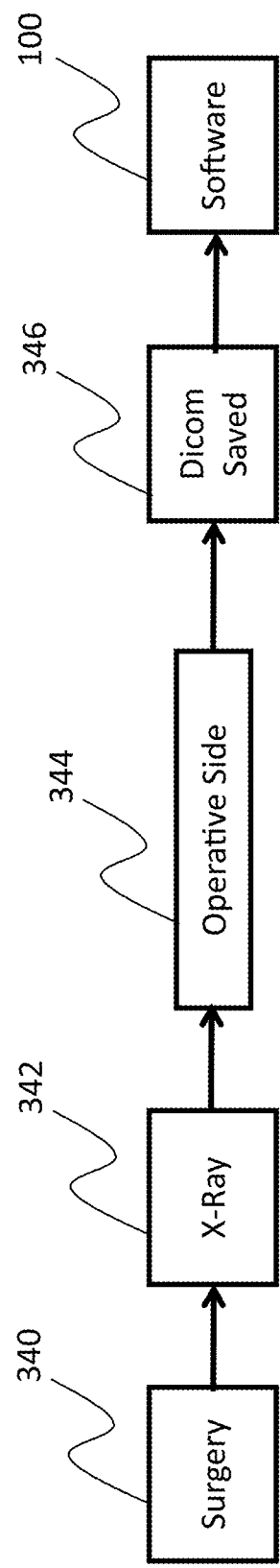
FIG. 11 is a block diagram of the intra-operative set up of the present invention.

Now referring to FIG. 11, the intra operative procedure is shown. The surgery (step 340) is conducted and an x-ray is taken of the operative side (steps 342 and 344) and a DICOM image is saved (step 346) and transmitted to software system 100 for analysis. In one embodiment, the digital x-ray image is continuously taken at a predefined interval during the entire operation.

Figure 12:
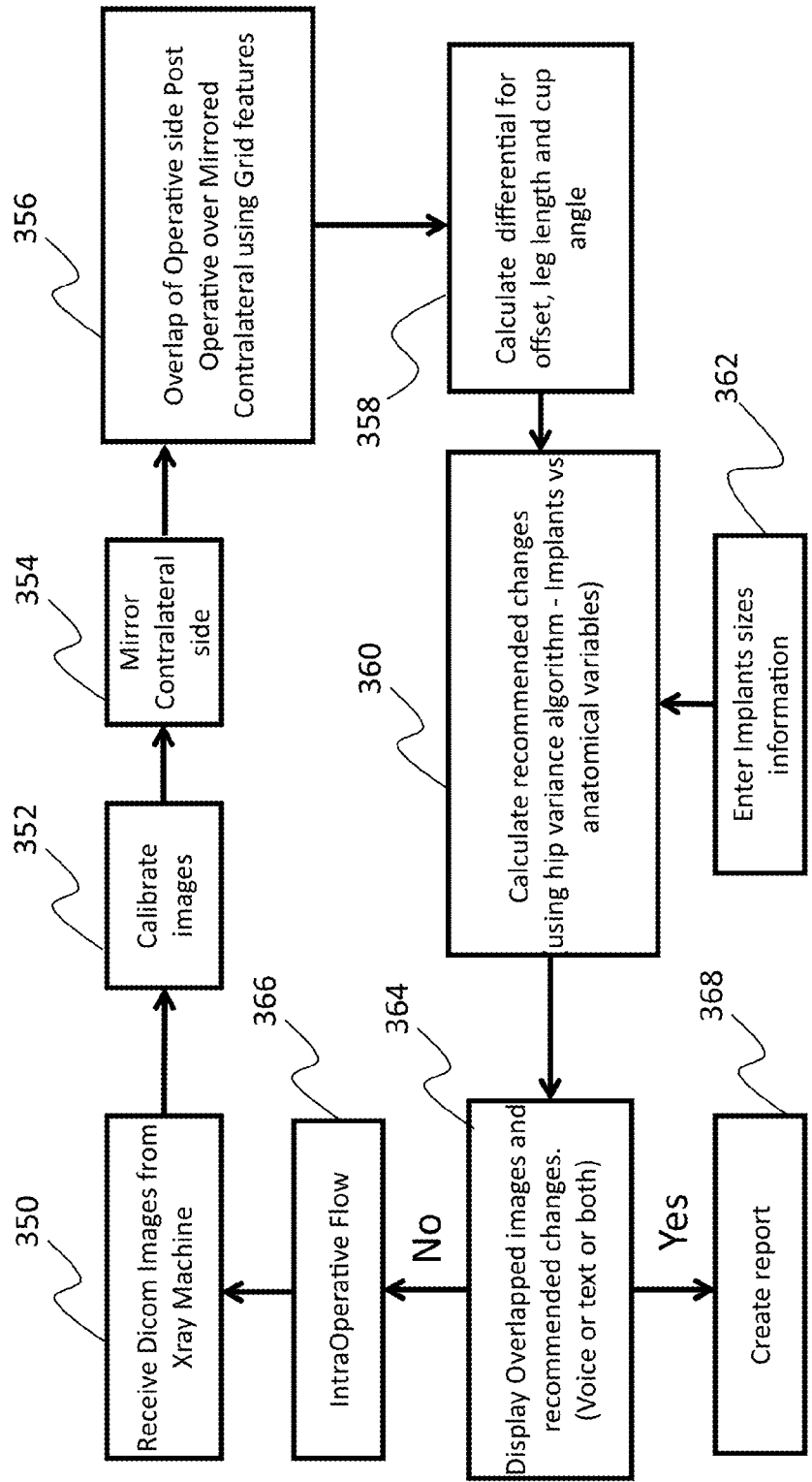
FIG. 12 is a block diagram of the overall architectural system of the present invention.

Now referring to FIG. 12, digital workflow of the software system 100 in one embodiment is shown. The software system 100 receives a DICOM image from C-Arm from the operative side, the images are calibrated. DICOM images of the contra lateral side are received. and calibrated. In another embodiment, DICOM images are received from an x-ray machine in step 350. Computer software system 100 processes the images and quantifies the magnification of the two images using markers and pixel-technology and calibrates the two images to same magnification in step 352. The contra lateral image is mirrored in step 354 and then overlaid for anatomy matching in step 356. Using grid plate apparatus 19 or 20, or using the internalized software algorithm grid, the overlap of the operative side and the mirrored contra lateral side is determined and shown.

The software system 100 aligns the two images together so that a pre-determined set of anatomic markers align one another in the overlaid image. It then makes measurements on a pre-defined set of parameters that are specific to surgical operation. By comparing the contra lateral image and the operative image, it then calculates the differences of these measurements in step 358 and then recommends changes in step 360. In one embodiment for hip surgery, the differential for off-set, leg length and cup are calculated. The software system 100 calculates the recommended changes using the hip variance algorithm implants vs. anatomical variables, and is also based on the input of implant size information that is entered in step 362. A display of overlapping images may be shown and the recommended changes are suggested in step 364. In a further embodiment, the recommendation may be presented in voice message or text message or both. If the system is operating in pre-operative mode, the software system 100 will follow the label YES and create a report to the surgeon in step 368. If it is operating in intra-operative mode, it takes the path labelled NO and follows step 366 back to step 350 again, where it takes another DICOM image and repeat the same digital flow to analyze the newly obtained DICOM operative image.

In one embodiment for a hip alignment, the C-arm image of both the left and right hips are saved (DICOM image), then calibrated (grid orientation are placed and orientated relative to the images). The digital images are overlaid one upon the other (of the two radiographic images) and then subsequent measurements and differences calculated (using pattern recognition technology/Pixel size technology). The differences related to implant position, offset, and other alignment parameters are determined based upon the calculations using a software algorithm and output provided for surgeons to use in determining accurate placement of the prosthesis.

Figure 20:
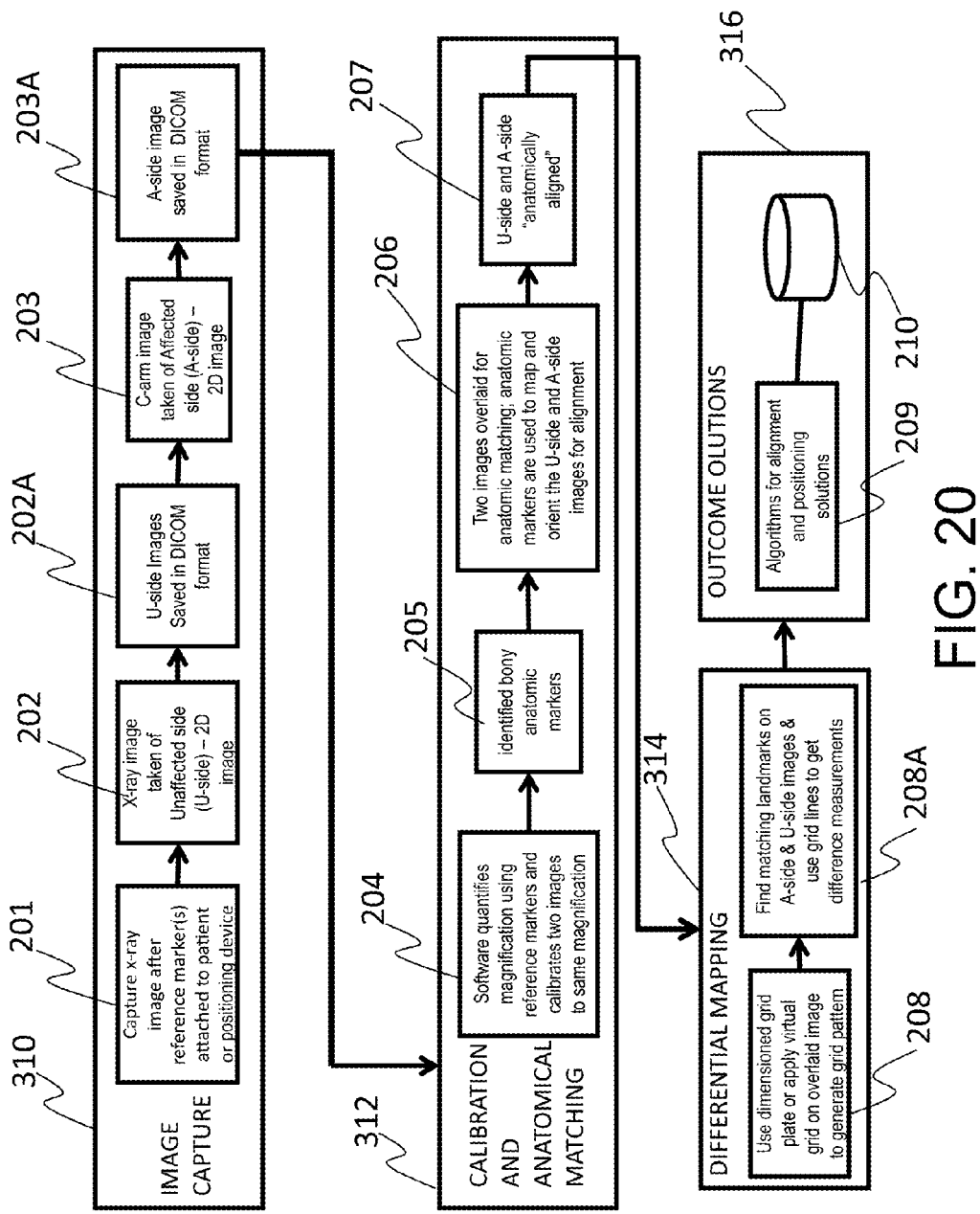
FIG. 20 is a software block diagram of the computer-aided surgical operation system in one embodiment of the present invention.

A detailed software flow diagram of the software system 100 is depicted in FIG. 20 in one embodiment. The software is organized into modules and each module has at least one function block as shown in this figure. The hip alignment embodiment mentioned above is used as an exemplary surgical procedure to illustrate the detailed operations of each block. It will be appreciated that the computer-aided surgical operation system disclosed here is not limited to perform only this surgical operation. For example, the present invention may be applicable to other musculoskeletal applications such as arthroplasty surgery for hip, knee, ankle and shoulder as well as trauma surgery for musculoskeletal repair. It will be clear to one skilled in the art that the present invention may be practiced with variations of the specific details described hereinafter.

In this embodiment, the software system 100 includes the image capturing module 310, the calibration and anatomical matching module 312, the differential mapping module 314 and the outcome solutions module 316. Firstly, at least one reference marker is affixed either to the patient or to a position device. These reference markers are used in function block 204 for orientation and magnification calibration. In one embodiment, the reference markers are placed on the patient. In another embodiment, they are attached to a patient positioning device, which is an apparatus that is used to keep the patient secure during a surgery operation. In both cases, the reference markers are located within the field of view of the x-ray detector so that they appear in the x-ray images that are to be taken in step 201.

Afterwards, an operator or a surgeon instructs the computer system 301 to take one or more radiographic images. The computer system 301 then invokes the image capturing module 310 to command the fluoroscopic machine to do so in function block 201. The fluoroscopic machine sends back a two dimensional x-ray image in DICOM format. In one embodiment an unaffected side of the hip (U-side) is taken (block 202) and saved (block 202A). Then a two dimensional x-ray DICOM image on the affected side of the hip (A-side) is also captured (block 203) and stored (block 203A). These two images are passed to the calibration and anatomical matching module 314 for analysis. The image of the unaffected side is referred to as the U-side image, the contra lateral image or simply the reference image while that of the affected side is also known as the A-side image or the operative image.

In the calibration and anatomical matching module 312, the first function block 204 is to calibrate the two images to the same magnification. This is done by using reference markers that are either attached to the patient or positioning device. Function block 204 will process the two images and determine magnification using the known marker dimension and then calibrate the two images to the same magnification.

Figure 21:
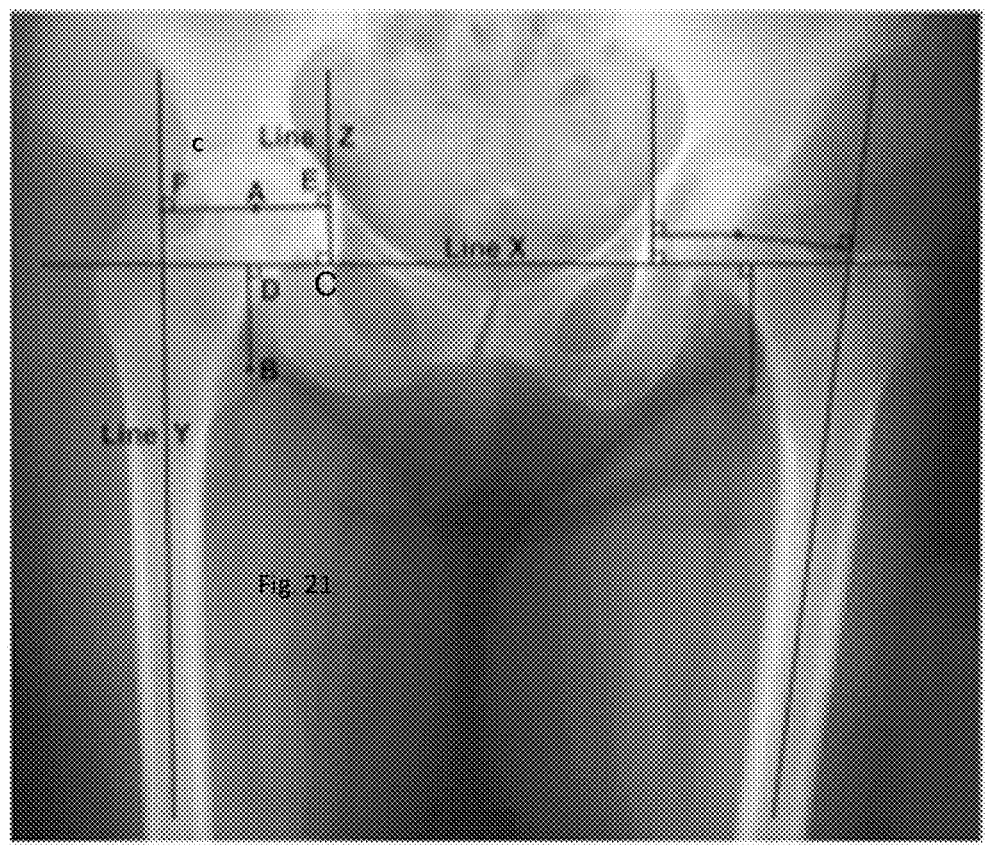
FIG. 21 is an x-ray image of a human hip showing some the anatomic markers.

After the images are calibrated, the anatomic markers of both the U-side image and the A-side image are obtained. FIG. 21 and the table below show a partial list of anatomic markers that may be used for total hip arthroplasty operation:

| Label as shown in FIG. 21 | Anatomic Markers |
| --- | --- |
| A | Hip rotation center |
| B | Lesser trochanter |
| C | Teardrop |
| FA | Femoral offset |
| AE | Acetabular offset |
| Line Y | Femoral shaft |
| Line X | Inter-teardrop line or Trans-teardrop line |
| Line Z | Perpendicular line to Line X at the most distal part of teardrop C |

Figure 22:
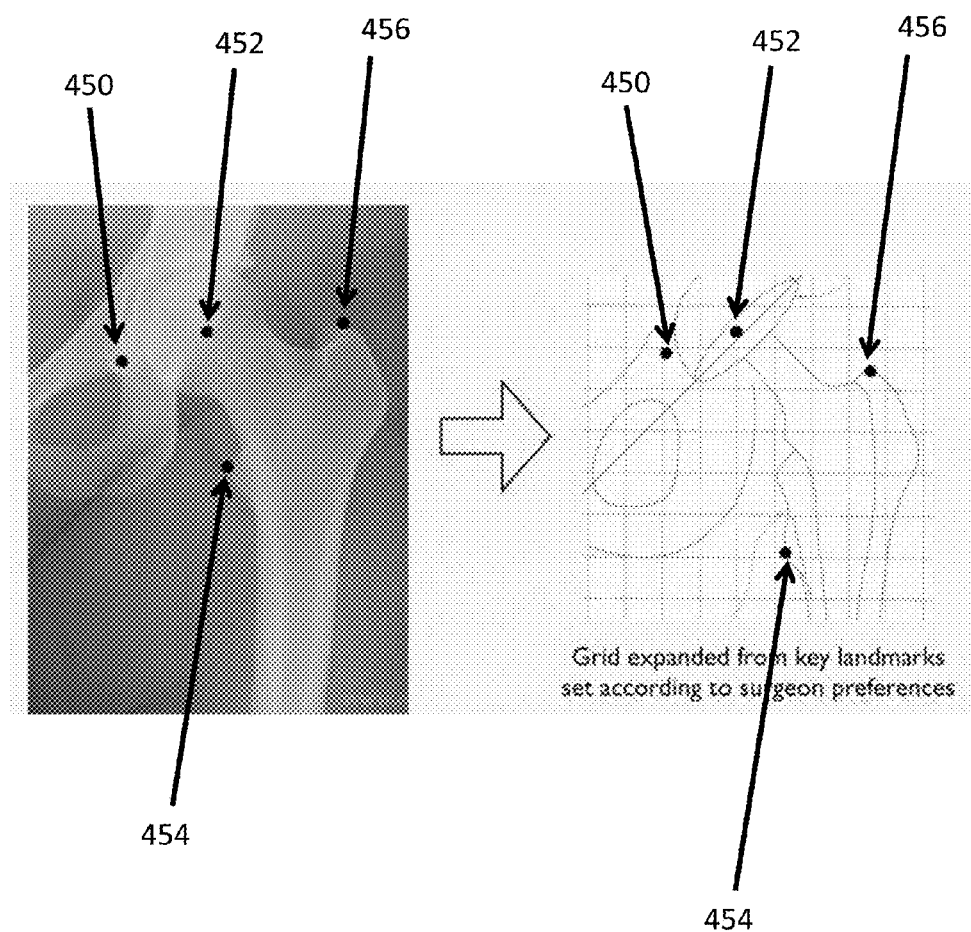
FIG. 22 is an exemplary illustration on how to identify the anatomic markers in one embodiment of the present invention.

In a further embodiment, at least one of these anatomic markers is identified for the anatomic matching operation. An exemplary example of how this is done is shown in FIG. 22. Here the teardrop 450, the hip rotation center 452, the greater trochanter 456 and the lesser trochanter 454 are chosen for matching. These anatomic markers may be chosen according to surgeon preferences. As shown in this figure, the bone contour in this x-ray image is traced and the corresponding anatomic markers are identified. This is done in function block 205 as described below.

Figure 23C:
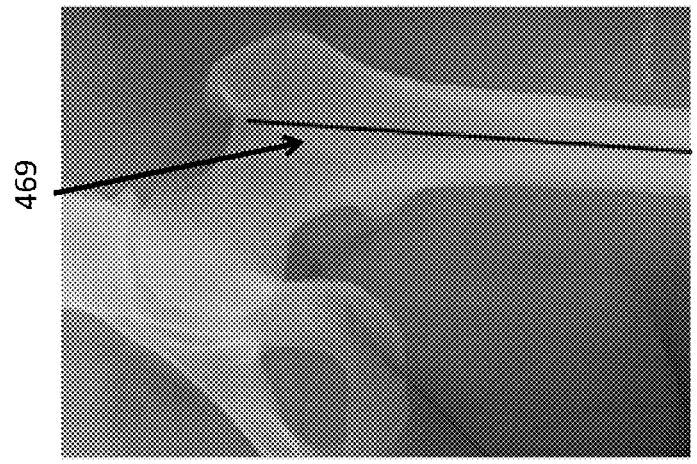
FIG. 23A to 23C illustrates the process of establishing the femur shaft anatomic marker on an x-ray image in one embodiment of the present invention.
Figure 23B:
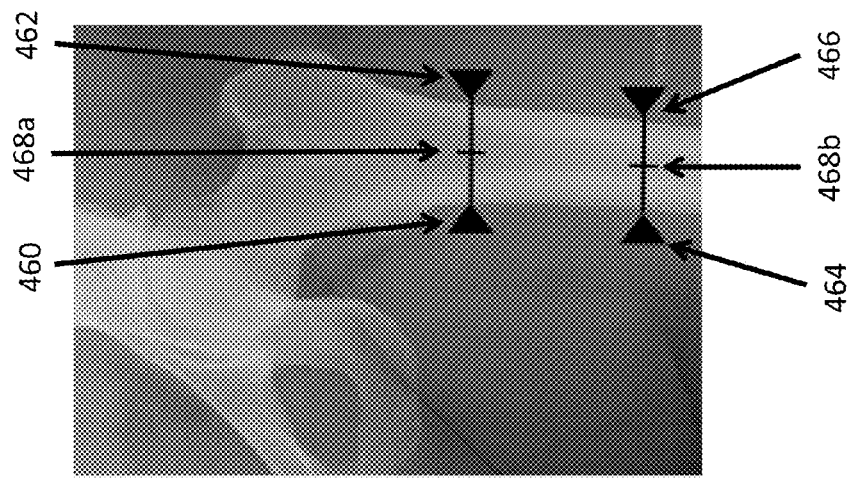
Figure 23A:
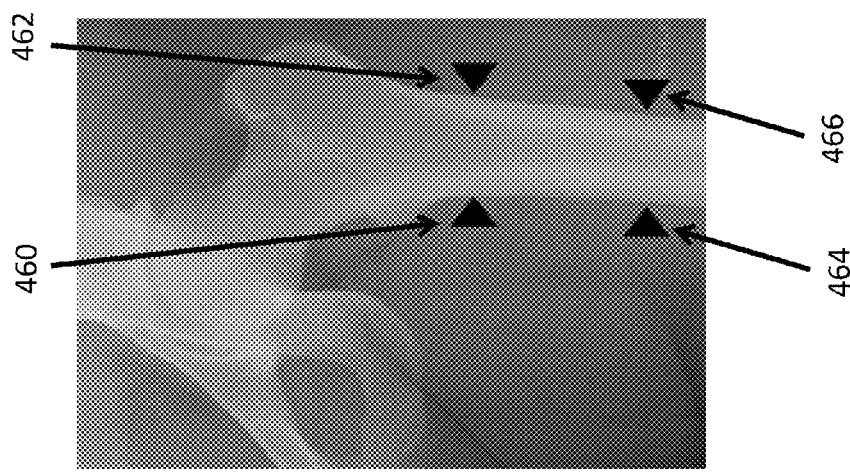

The anatomic markers can be identified by the surgeon manually (by point and click onto the monitor screen that is displaying the corresponding x-ray image), or by the computer software automatically using pattern recognition technique. In one embodiment, it uses pixel size and gray contrasting to define geometrical patterns. For example, the head has a pixel shade relative to the surrounding anatomy and the software defines the border based upon contrast. FIGS. 23A to 23C illustrates how a femoral shaft is automatically determined by software. Firstly, the edge of the medial and lateral cortex is determined by examining the pixel contrast in at least four locations (460 and 462; 464 and 466 in FIGS. 23A and 23B) along the proximal/distal plane. The distance between the medial and the lateral cortex is measured and is equally split to find the mid-points (468a and 468b). The femoral shaft 469 can then be obtained by drawing a straight line that passes through the mid-points (468a and 468b). Other anatomic markers can also be automatically recognized by similar image processing and pattern recognition techniques. For example, pixel shading and gray contrasting, methods such as random forest regression, hierarchal sparse shape recognition, edge/region/shape detection, anatomical feature thresholding or clustering techniques, or any combination of the above can be used. In a further embodiment, a special pattern recognizer can be developed to recognize each individual anatomic marker or associated anatomical geometrical structure. For example, the teardrop has a unique shape and its orientation and size and general relative geometrical position does not vary greatly among patients. As such, a special recognizer can be built to identify this anatomic marker reliably using statistical pattern recognition technique.

Figure 24A:
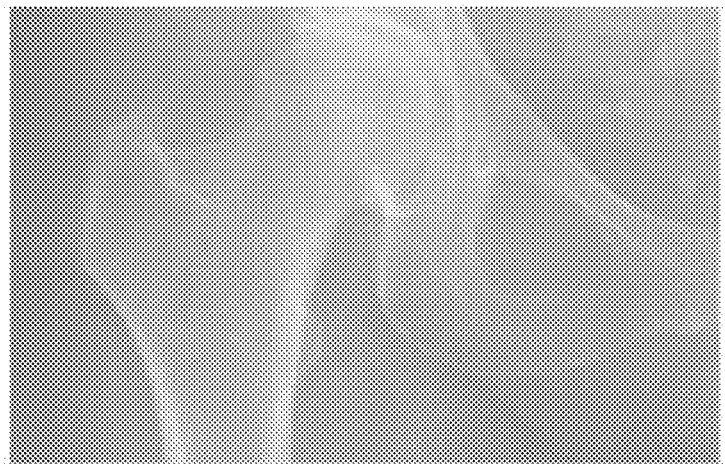
FIG. 24A is a contra lateral x-ray image of a patient's hip in one embodiment of the present invention.
Figure 24B:
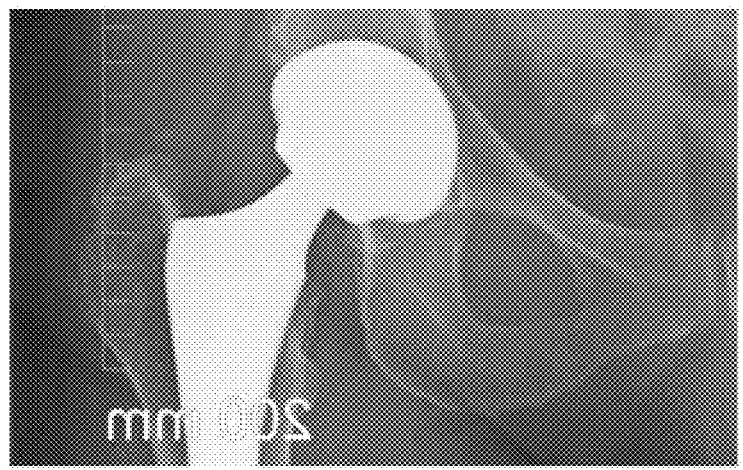
FIG. 24B is an operative x-ray image of the patient's hip in one embodiment of the present invention.
Figure 24C:
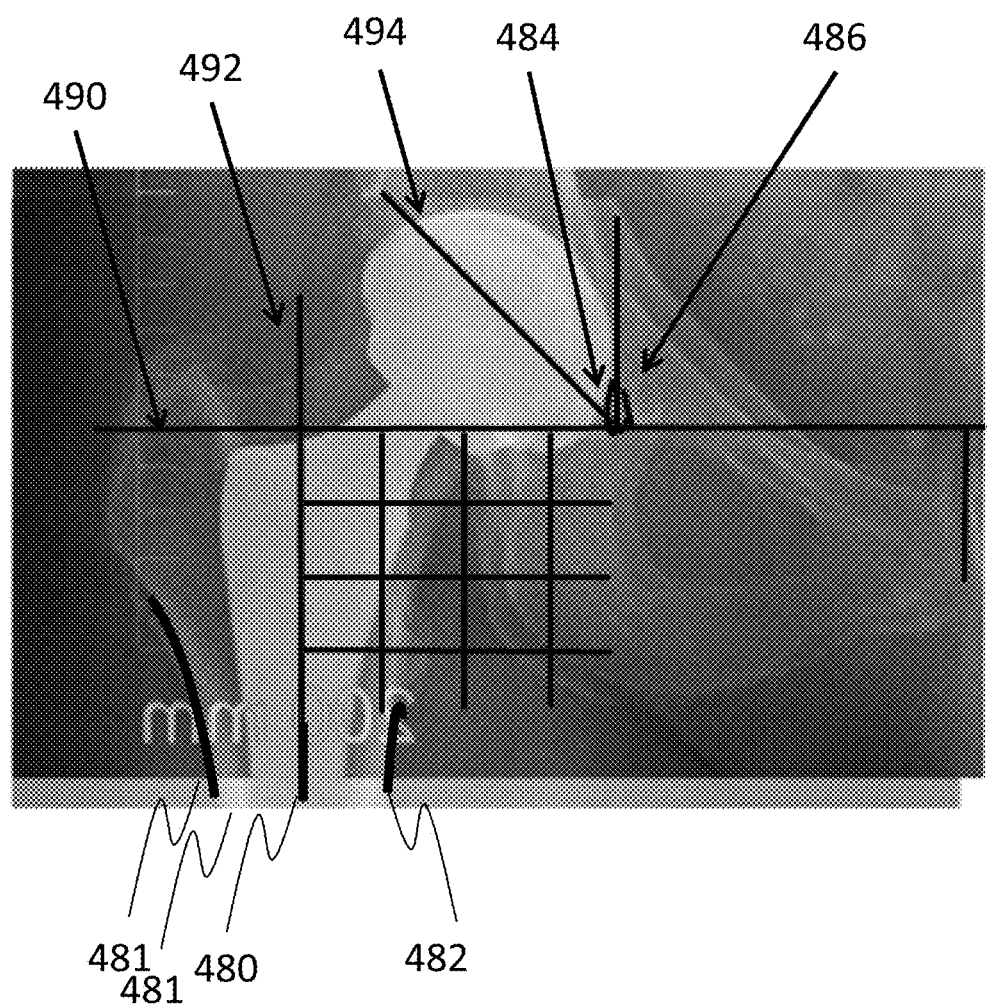
FIG. 24C illustrates an overlaid image after the contra lateral image is overlaid onto the operative image and the appropriate anatomic makers are aligned in one embodiment. This figure also shows a virtual grid superimposed onto the overlaid image.

After the anatomic markers are found, one of the images is flipped 180 degree so a mirrored image is obtained and overlapped on the other image in block 206. As an example, FIG. 24A shows a mirrored U-side image and FIG. 24B depicts an A-side image having the implant already inserted. When the two images are overlaid, anatomic markers that are previously identified are used to align the two images so that the essential features overlap each other in the overlaid image as shown in FIG. 24C. This is done in in function block 207.

The overlaid image is then sent to the differential mapping module 314 for analysis and measurement. In one embodiment, software generated virtual grid having a unique grid pattern for a specific surgical operation is generated and is superimposed or overlaid onto the overlaid image in block 208. Then the key matching anatomical landmarks on the A-side image and the U-side images are identified in block 208A. This function block further calculates the relative distances from the grid to these landmarks and then computes at least one measurement based on the differences of the relative distances. The at least one measurement is then forwarded to the outcome solutions module 316 for further processing.

To further explain the detailed operations of differential mapping, an exemplary measurement procedure on total hip arthroplasty is discussed below. Referring to FIG. 24C, the virtual grid includes the inter-teardrop (or trans-teardrop) line 490, a femoral shaft line 492, a diagonal line 494 for cup abduction angle measurement and a plurality of horizontal lines and vertical lines forming a grid pattern. The virtual grid is first aligned with the anatomic markers. In this case, the femur of the A-side image and the U-side image are first aligned in block 207. This is indicated in FIG. 24C where the boundaries 481 and 482 of the femur in two images overlap each other. However, the teardrop 484 of the A-side image does not fully overlap the teardrop 486 of the U-side image. The software then aligns the femoral line 492 of the virtual grid to the femoral shaft 480, and the inter-teardrop line 490 to the horizontal line that joins the distal tips of teardrops 484 and 486. With that, the relative distance between the two teardrops can be measured with the help of the grid pattern. In one embodiment, the anatomic markers vital to the surgical operations are referenced by the grid coordinates as shown in FIG. 9. The distance between an A-side anatomic marker against the corresponding U-side anatomic marker can then be quantified using the grid coordinate as a guide.

Figure 25:
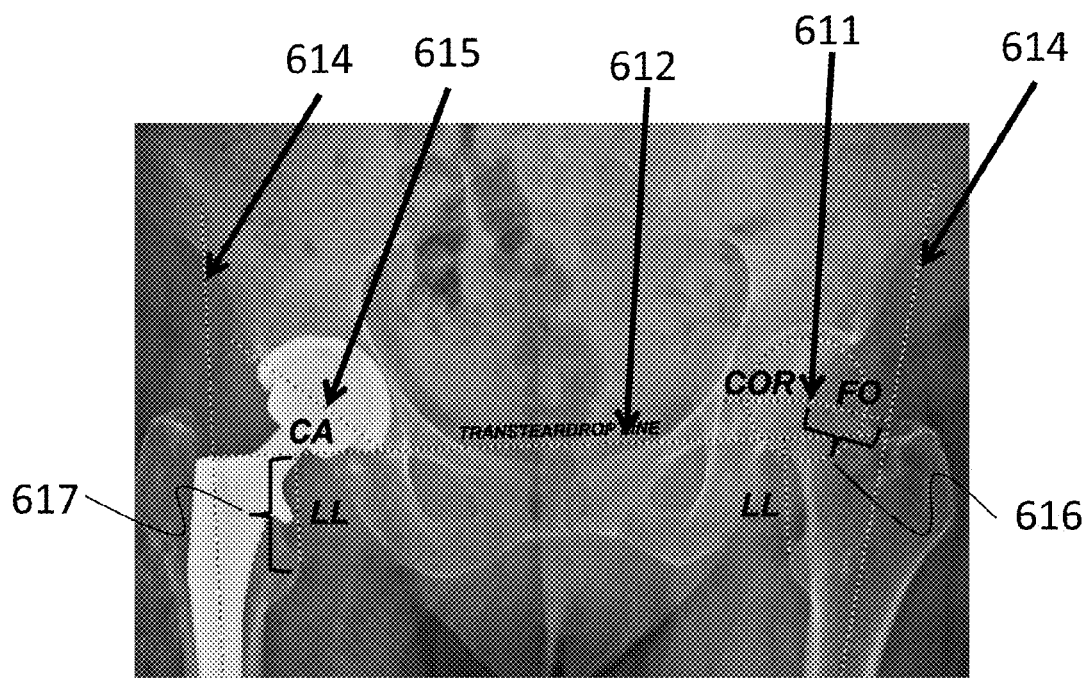
FIG. 25 shows another virtual grid superimposed onto another x-ray image of a patient's hip. in another embodiment of the present invention.

Various virtual grids can be used, depending on the preference of the surgeon. FIG. 21 and FIG. 25 are other software-generated virtual grids that may be used for total hip arthroplasty (THA). Referring to FIG. 25, the center of rotation (COR) (or hip rotation center) 611, the trans-teardrop line 612, the femoral shaft 614, the leg length (LL) 617, the femoral offset 616 and the cup abduction (CA) 614 are identified and constructed either manually or automatically. These points and lines form the virtual grid in this particular embodiment.

Figure 26:
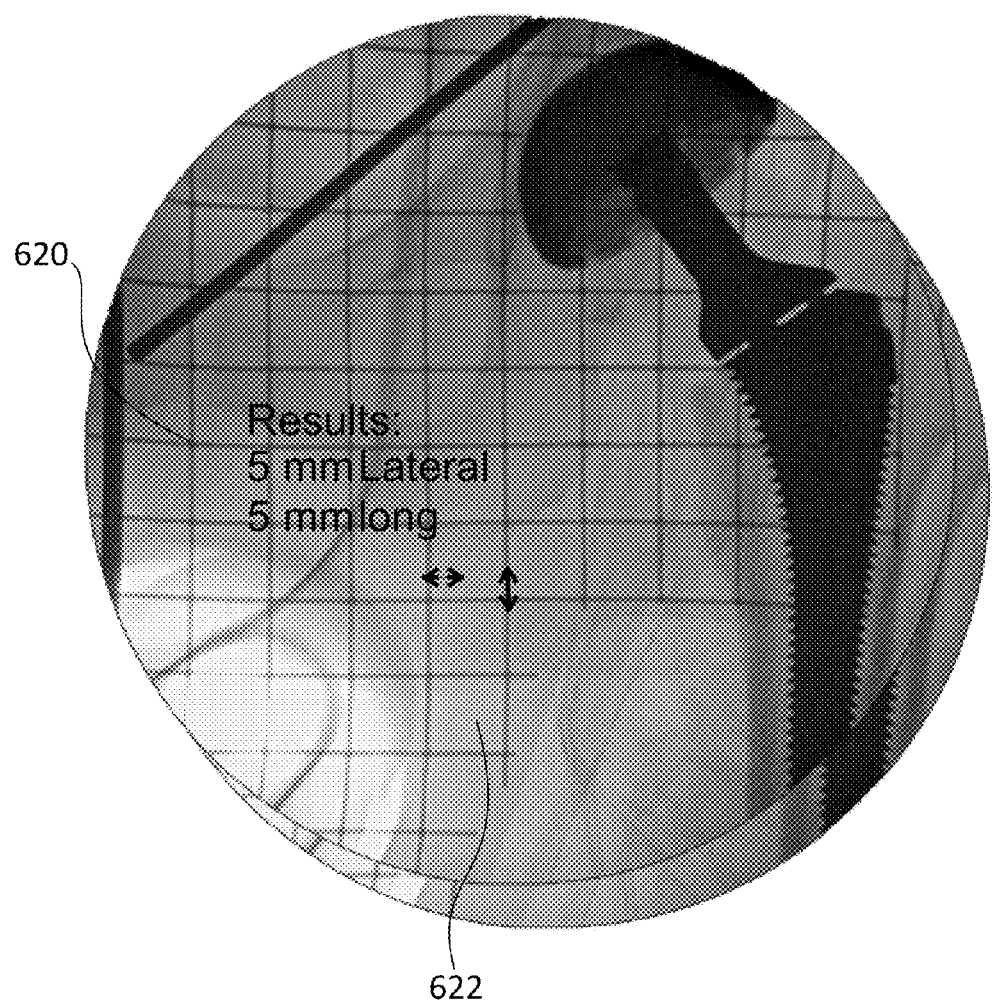
FIG. 26 shows an overlaid image wherein both the operative image and the contra lateral image are taken with a dimensioned grid placed between the patient and the x-ray detector. Hence the dimensioned grid pattern appears on both images.

In another embodiment, the dimensioned grid plate 19 is used for creating the grid pattern(s) on the overlaid image. In this case, the dimensioned grid plate 19 is placed in between the patient 27 and the x-ray detector 602 as shown in FIG. 6B. In this scenario, the image capturing module will capture the grid pattern of the dimensioned grid plate. As such, a reference grid pattern appears on the U-side image and an operative grid pattern appears on the A-side image. When these two images are overlaid and anatomically aligned, the respective grid patterns are superimposed onto the overlaid image too, resulting a composite grid pattern as shown in FIG. 26. As shown in this figure, the composite grid pattern consists of one grid 620 from one image (with darker color) and another grid 622 from another image (with lighter color). The displacements between the grid patterns can then be measured. In this figure it indicates that the horizontal (lateral) displacement and the vertical displacement are both 5 mm. As such, when an anatomic marker in the A-side image is referenced by the A-side reference grid coordinate, and the corresponding anatomic marker in the U-side image is referenced by the U-side operative grid coordinate, the relative distance between the two markers can be readily calculated based on the difference of grid coordinates as well as the displacements between the two grid patterns. For example, if an A-side marker is marked as G6.5 on the A-side reference grid coordinate and the corresponding U-side marker is G5.5 on the U-side operative grid coordinate, then there is a horizontal distance of one unit (6.5-5.5). The actual distance will be adjusted by the 5 mm displacement between the A-side grid and the U-side grid in this case.

Whether a virtual grid is used or a physical dimensioned grid plate is chosen in the differential mapping module 314, this module produces at least one measurement, which indicates the displacement between the A-side anatomic part against the corresponding U-side anatomic part that is vital to the operation. This at least one measurement in effect quantifies the difference between the two anatomic parts and provide feedback to the surgeon on how much he needs to correct to restore correct implant placement and alignment. In one embodiment, the vital measurements for the total hip arthroplasty are the leg length, the offset and the cup placement. The measurements are then passed to the outcome solutions module 316.

The outcome solutions module 316 presents at least one measurement of surgical variables involving the implant to the surgeon. This facilitates the placement of the implant in the patient. In one embodiment, this module includes a function block 209 that contains algorithms for alignment and positioning solutions. In the embodiment for total hip arthroplasty (THA), a hip-variance algorithm can be used. Now referring to FIGS. 13-15 wherein in the hip-variance algorithms are explained. FIG. 13 is a table specifying what surgical adjustment(s) are needed when the leg length is in one of the short, good, or long categories while the offset is either medial, good or lateral. Accordingly, the table has nine entries for all the nine possible combinations. Each entry specifies an appropriate surgical procedure for the surgeon to consider. For example, if the leg length is found short and the offset is medial, then the algorithm recommends adding head length and upsize stem.

Figure 14:
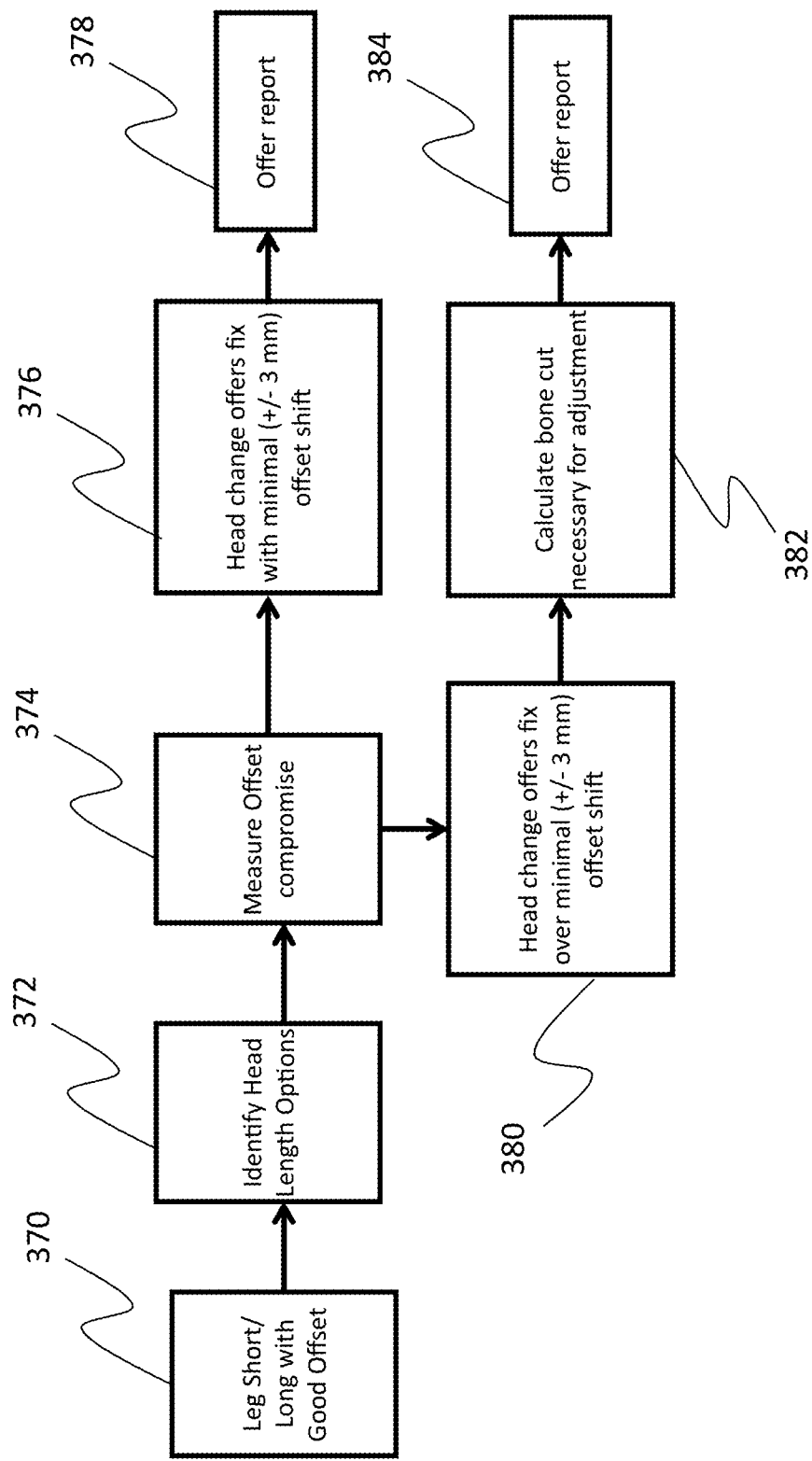
FIG. 14 is a block diagram of the Hip Variance Algorithm the present invention.
Figure 15:
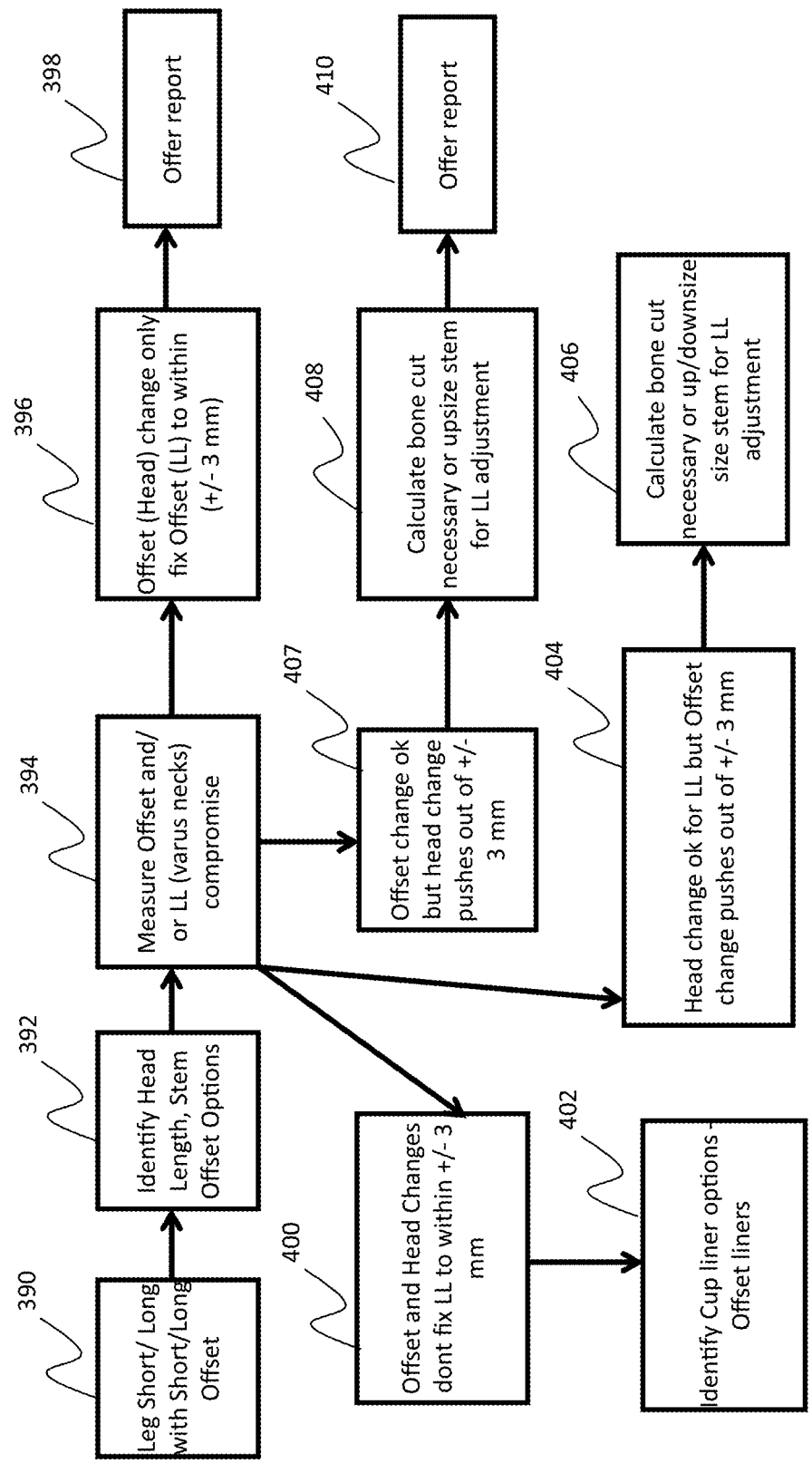
FIG. 15 is a block diagram of the Hip Variance Algorithm the present invention.

In a further embodiment, FIG. 14 and FIG. 15 translate the table entries as shown in FIG. 13 into surgical actions and recommendations to the surgeon. FIG. 14 shows the case where the offset is good but the leg length is either short or long. If that is the case, step 370 is entered. The algorithm then identifies the head length option in step 372 and then measure the offset compromise (step 374). If the leg length is found to be short, then step 376 is taken, and the head change offers fix with minimal (+/−3 mm) offset shift. A report will then be issued in step 378. If the leg length is categorized as long, then step 380 is taken followed by step 382, which is to calculate bone cut necessary for adjustment. Then a report will be sent out in step 384.

FIG. 15 shows the four cases whereby the leg length is either short or long while the offset is either medial or lateral. The algorithm is entered in step 390. It first identifies the head length and stem offset options in step 392. Then the offset and/or leg length are measured in step 394. Depending on the measured result, one of the following four procedures are recommended:
If leg length is short and offset is medial, then follow steps 400 and 402;
If leg length is short and offset is lateral, then follow steps 396 and 398;
If leg length is long and offset is medial, then follow steps 407. 408 and 410;
If leg length is long and offset is lateral, then follow steps 404 and 406;

The outcome solutions module 316 stores many different algorithms and procedures in its database 210 for different surgical operations, of which the hip variance algorithm is one of them for the total hip arthroplasty operation. Depending on the surgical operations to be performed, different algorithms or procedures will be invoked. For example, for knee, shoulder and ankle arthroplasty and trauma fracture reduction and fixation surgery, specific algorithms designed for that surgical operation will be executed.

In one embodiment, detailed operational procedures for various cup navigation applications are described below to further illustrate the merits of the present invention.

FIG. 27A shows, a series of x-ray images of a pelvis wherein an original standing Anterior Posterior (AP) Pelvis x-ray saved within the software pre-operatively is used as an overlay reference intra-operatively so that the surgeon can properly identify the natural standing position of the pelvis prior to commencement of the implantation process. Each intraoperative image is automatically overlaid over the original image until a matching anatomical view is reached and deemed acceptable by the surgeon to proceed.

Firstly, a pre-operative, digitally-templated x-ray of a standing AP pelvis is loaded into application as shown in FIG. 27A-1. Then, an intraoperative image of the same patient AP pelvis is taken and loaded into the software.

The application takes sequential intraoperative x-rays (FIG. 27A-2 to FIG. 27A-4) and overlays them over the pre-operative x-rays to determine the actual patient pelvis tilt angle. (This is important as the cup angulation must be position as it relates to the anatomy in its functional intended position. Since the patient is laying down, the proper pelvis position must be identified before the implant is implanted).

The position of the x-ray machine needs to be identified so as to display the "standing" view of the pelvis PRIOR to displaying any digitally-produced pattern (Grid or other relevant pattern) used for navigation of implants (i.e. in the case of a total hip).

FIG. 27B illustrates another process by which the application can establish the proper intraoperative determination of a patient's standing pelvic tilt using the inlet measurement as applied to intraoperative x-ray images. A pre-operative, digitally-templated x-ray of a standing AP pelvis is loaded into application. Using trigonometric mathematics and formulas such as described by Pradhan (JBJS (Br) 1999), Liaw, et al. (Journal Arthroplasty 2009), the software can calculate and determine a pelvic tilt or "A-P version". The application determines the inner diameter of the pelvis ring by identifying the most lateral portion of its inner ring. Then it determines the distance from that diameter to the identified symphysis pubis. By projecting that distance directly opposite and at equidistance over, an elliptical shape is determined (FIG. 27B-1). Using trigonometric mathematics and formulas, a pelvic tilt angle/version is determined for that patient.

An intraoperative image of the same patient AP pelvis is taken (FIG. 27B-2) and loaded into the software. The application then takes sequential intraoperative x-rays of the pelvis and processes each image with the same calculation until the intraoperative view's determined pelvic tilt version match the pre-operative version. (FIG. 27B-3 to FIG. 27B-4)

Figure 28:
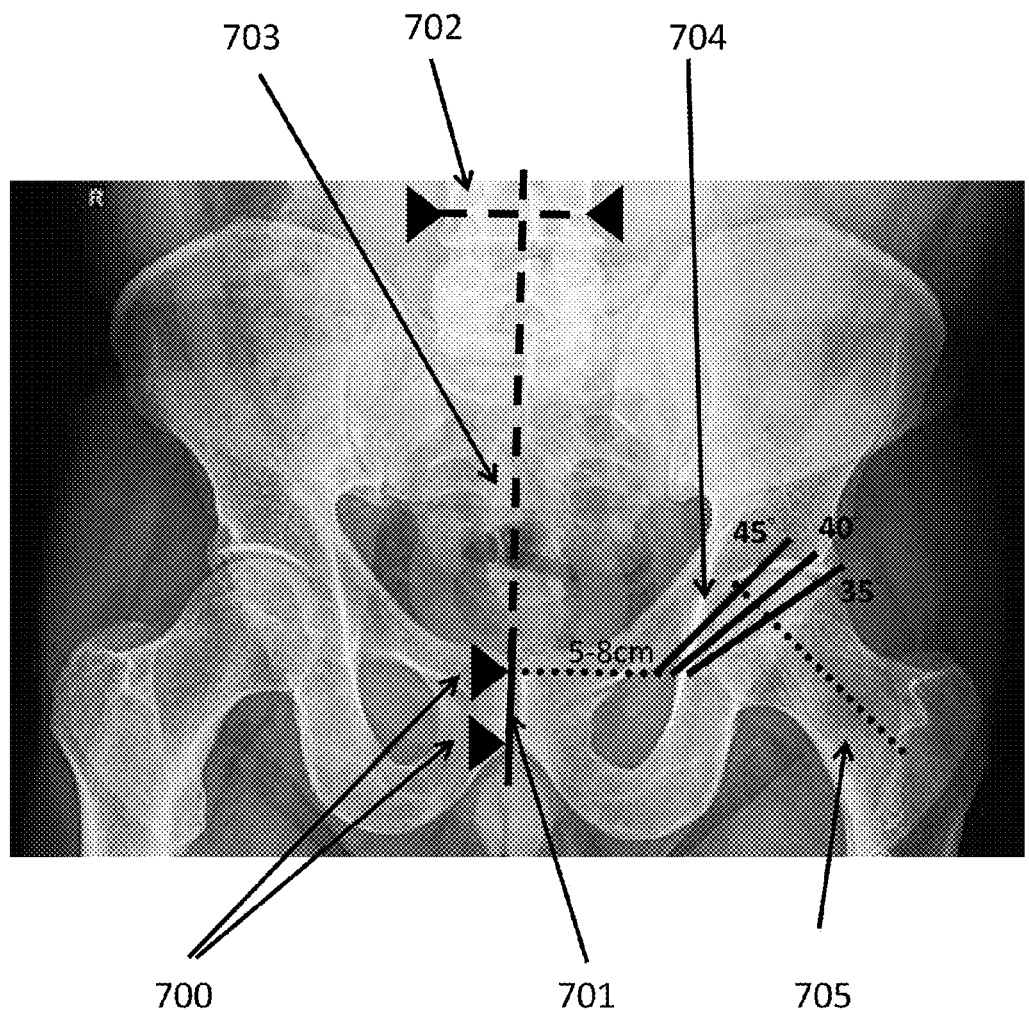
FIG. 28 illustrates the process of establishing symphysis pubis anatomical marker on one embodiment of the present invention.

FIG. 28 illustrates the process of establishing symphysis pubis anatomical marker on one embodiment of the present invention. It includes the following steps:

Step 1 (700)—Identify either manually or with pattern recognition method the superior edge and the inferior edge of the symphysis Pubis (SP).

Step 2 (701)—Use these two points to determine the superior-inferior axis of the pelvis.

Step 3 (702)—Identify either manually or with pattern recognition method the lateral co-facing edges of at least one vertebrae. Use the perpendicular at the medium to offer a visual (dash) line to the user.

Step 4 (703)—Using the rotation of the x-ray machine, the user can rotate its view of the pelvis until the spinal alignment line and the pubis line are superposed or each anatomical axis is in the same sagittal plane (SP).

Step 5 (704)—Project 5 cm to 8 cm lateral from the superior edge of the SP of the central axis and obtain a set of angled lines at the following angles 45°, 40°, 35°. (Note: true angles of the central axis are: 45°, 50° and 55° but for display purposes, it should show as the prior because of standard anatomical nomenclature).

Step 6 (705)—Project a perpendicular line from either of the desired (preference setting in the application) previously projected angled lines to be used for direction of the navigation of an instrument such as a reamer or cup impactor handle. By visually assessing that line, a user can navigate its cup abduction angle.

Figure 29:
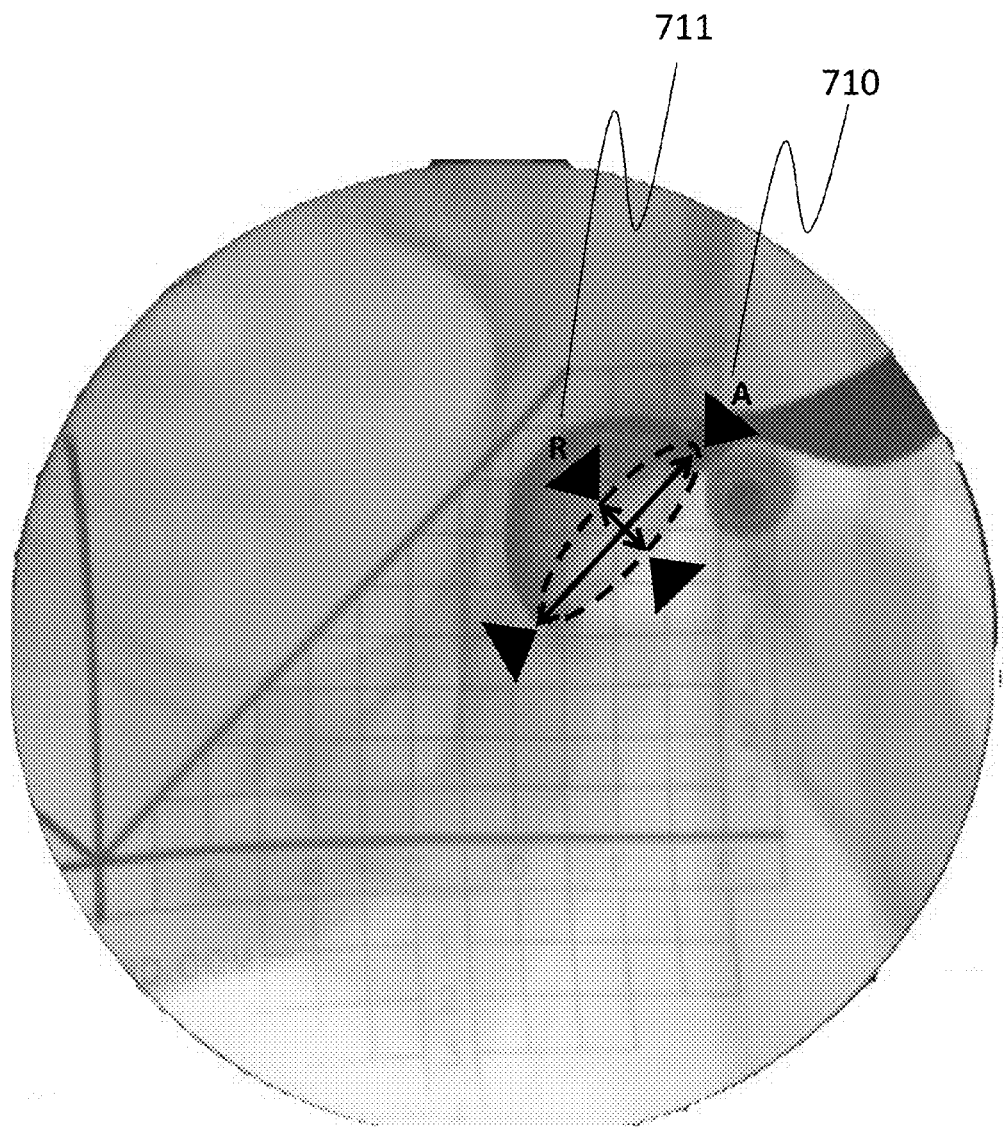
FIG. 29 illustrates how using trigonometric mathematics and formulas the software can calculate and determine the version of the cup.

FIG. 29 illustrates how using trigonometric mathematics and formulas such as described by Pradhan (JBJS (Br)

1999), Liaw, et al. (Journal Arthroplasty 2009), the software can calculate and determine the version of the cup. The details of the formulas can be found in the respective articles and are not repeated here. The procedure is as follows:

Step 1—Identify either manually or with pattern recognition method the superior edge and the inferior edge of the acetabular cup. Label A 710 in FIG. 29 is a known dimension which is the diameter of cup implant.

Step 2—Identify either manually or with pattern recognition method the center distance of the opening of the cup (label R 711).

Step 3—Measure R.

Step 4—Measure angle opening with Pythagorean theorem.

In another embodiment, the outcome solutions module further includes additional functionalities. It includes, but not limited to the following: 1) visual display of comparative tools such as any grid design or other relevant pattern, implant specific specifications (templates), and other data for visual and/or quantification purpose; 2) Individual surgeon settings enabling the surgeon to input his preference, 3) multiple module options such as hip, knee, trauma etc, for different surgical operations 4) Data management such as collecting, tracking, and reporting features/functions for outcomes data, and quality matrix for data analysis and reimbursement, 5) Use of external additional references either as markers or any grid pattern (grid line, letter etc) to work in conjunction with the application, 6) Various surgical planning functions such as notes, templates, preferences, ordering, case lists to help surgeon in his surgical planning, and 7) Implant delivery tracking and billing functions.

Figure 30:
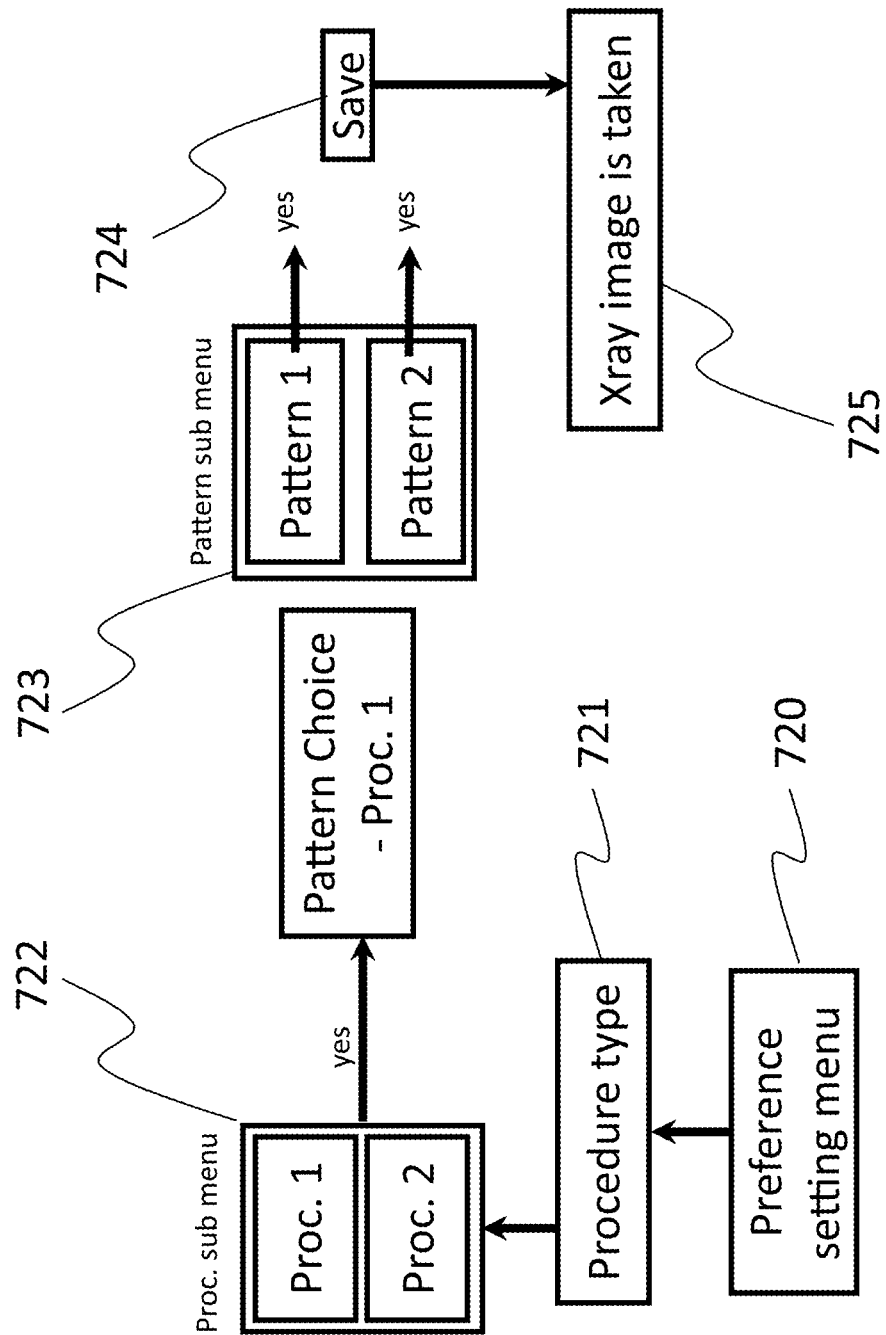
FIG. 30 is a software block diagram illustrating the use of a menu of procedures and related patterns or grid-patterns for a user to preselect prior to taking x-ray images so as to display these patterns automatically over the x-ray using each pattern specific algorithm for calculation and display.

FIG. 30 is a software block diagram illustrating the use of a menu of procedures and related patterns or grid-patterns for a user to preselect prior to taking x-ray images so as to display these patterns automatically over the x-ray using each pattern specific algorithm for calculation and display. Firstly, the preference setting menu (step 720) and the procedure type is selected (step 721). Depending on the selection, the procedure submenu is entered in step 722. A sequence of patterns is pre-selected (step 723) according to surgeon and procedure type with the intention to be used in a sequential manner. The selection sequence is saved in step 724 and then the x-ray sequence is taken in step 725.

Figure 31:
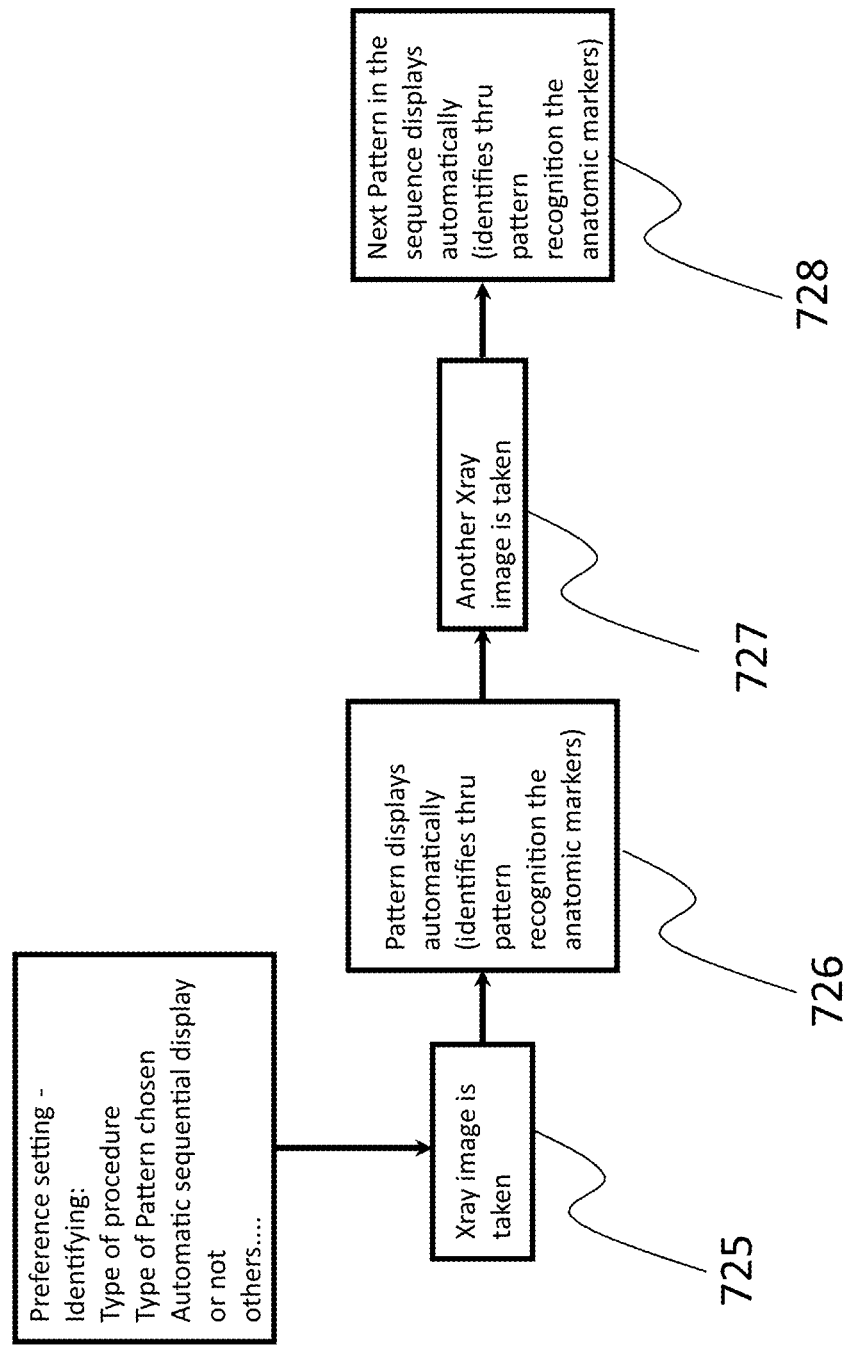
FIG. 31 is a software block diagram illustrating the use of preset preferences to automatically display a series of patterns over a digital x-ray by using the detection of a new x-ray image as the command to display the next pattern in the series of patterns.

FIG. 31 is a software block diagram illustrating the use of preset preferences to automatically display a series of patterns over a digital x-ray by using the detection of a new x-ray image as the command to display the next pattern in the series of patterns. After the process as described in FIG. 30 is taken, an image is taken in step 725. In one embodiment, anatomic markers are identified and the pattern displayed automatically and superimposed onto the image in step 726. When subsequent images are taken in step 727. The anatomic markers on the newly acquired image are identified and the pattern displayed automatically again in step 728.

In yet another embodiment, the computer system 310 may further be augmented by an integrated modules that may include: training and education functions for new users such as: 1) technique step display, 2) tips and pearls of proper surgical technique, 3) reminders between steps, 4) image gallery for reference, 5) image and video recording functions for review and/or broadcast.

The computer-aided surgical operation system disclosed in previous paragraphs is one of the many ways to implement the present invention. An alternative embodiment is presented in the following paragraphs. Those skilled in the art may develop other system configurations based on the teaching of this specification but yet they will be covered by this invention disclosure.

Figure 16:
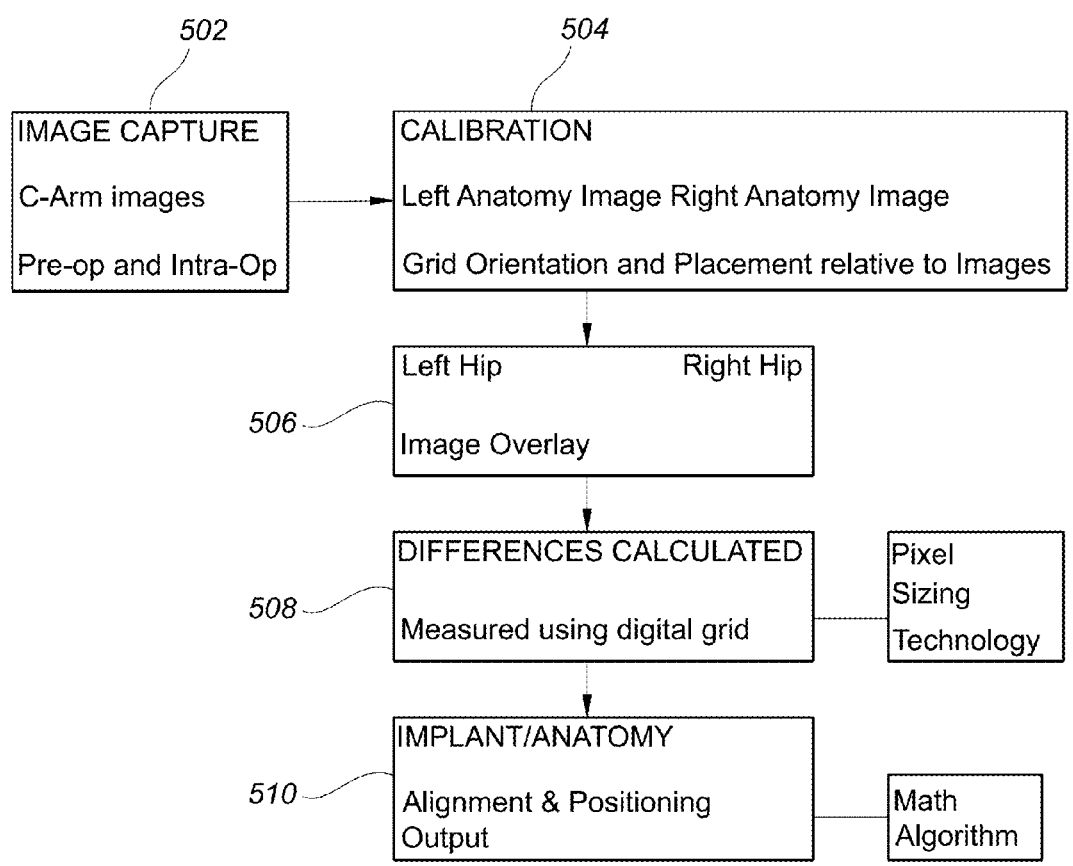
FIG. 16 is a block diagram of the image capture and calibration process the present invention.
Figure 17:
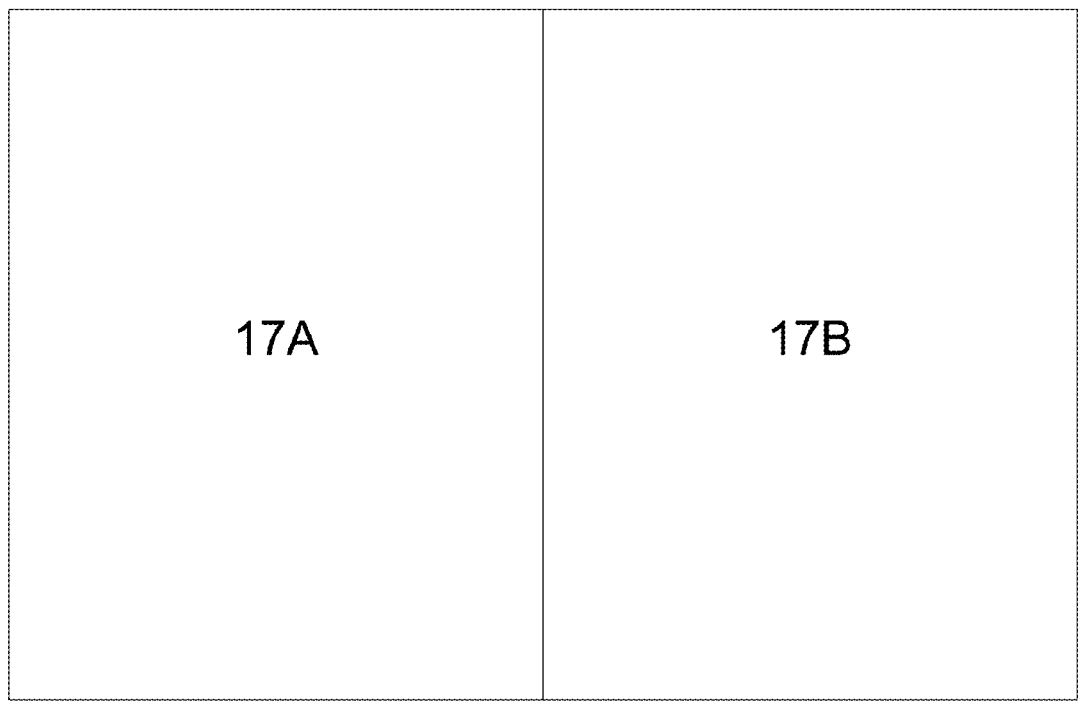
FIG. 17 is another block diagram of the image capture and calibration process the present invention.
Figure 17A:
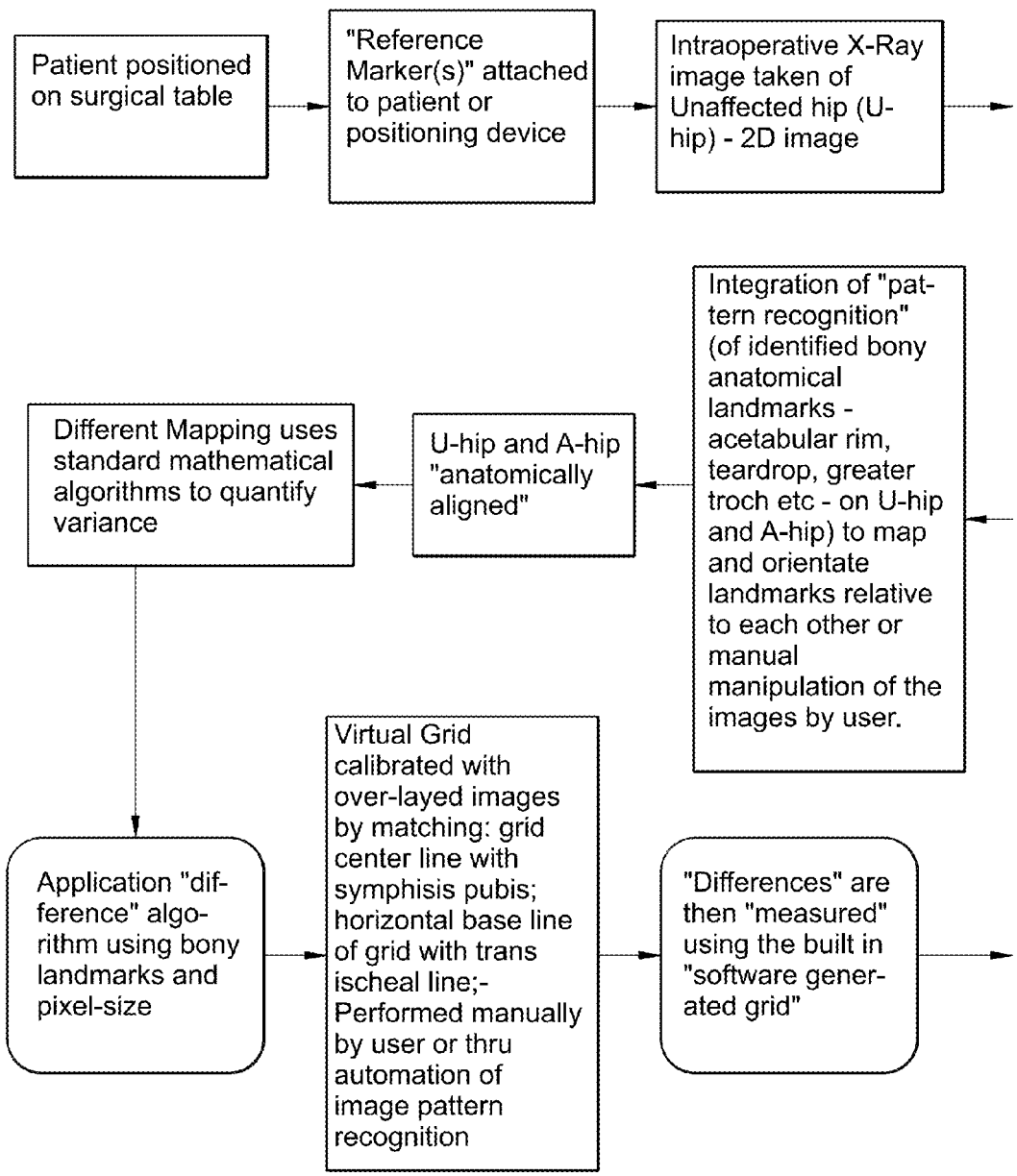
Figure 17B:
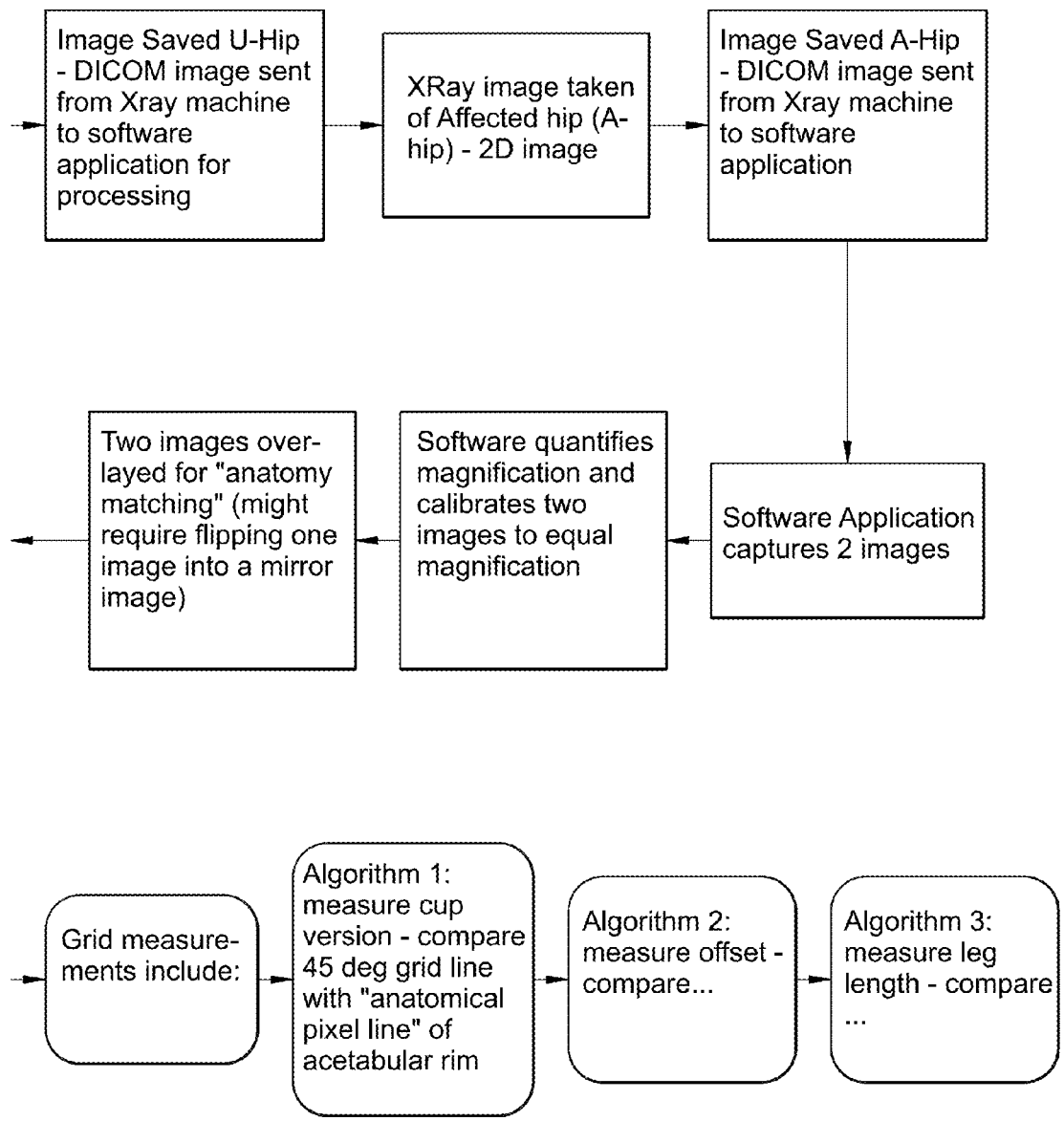

Now referring to FIGS. 16-17, the digital calibration process is shown between the image capture and calibration in an alternative embodiment. A patient is placed on a surgical table and reference markers are attached to the patient or the position device. In step 502, a C-arm image is taken of the affected hip (U-hip) and is saved. This first image is sent to the pattern recognition software. A C-arm image is taken of the unaffected hip (A-hip) and is saved. This second image is sent to the pattern recognition software. These first and second images are captured. Using markers, the two hip images are calibrated to the same magnification in step 504. In step 506 the two images are over-layed for matching anatomy. The pattern recognition of identical bony anatomical landmarks such as the acetabular rim, teardrop, and greater trochanter on the U-hip and A-hip are used to map and orientate the landmarks relative to each other. The U-hip and the A-hip are anatomically aligned and then differentially mapped. A virtual grid is calibrated based on the difference algorithm using bony landmarks and pixel size. The virtual grid is calibrated with over-layed images by matching the grid center line with symphisis pubis or teardrop line, and horizontal grid line with the trans ischeal line. In step 508 the differences are then measured using a software generated grid. The grid measurements include a series of algorithms: algorithm 1 measures cup version and compares the 45 degree line with the anatomical pixel line of the acetabular rim; algorithm 2 is the measured offset and algorithm 3 is the measured leg length. In step 510, the alignment and positioning parameters are then output. FIG. 17 is a digital process flow of this alternative embodiment. This flow diagram is very similar to the one shown in FIG. 20 and its operation details are not repeated here.

Figure 18:
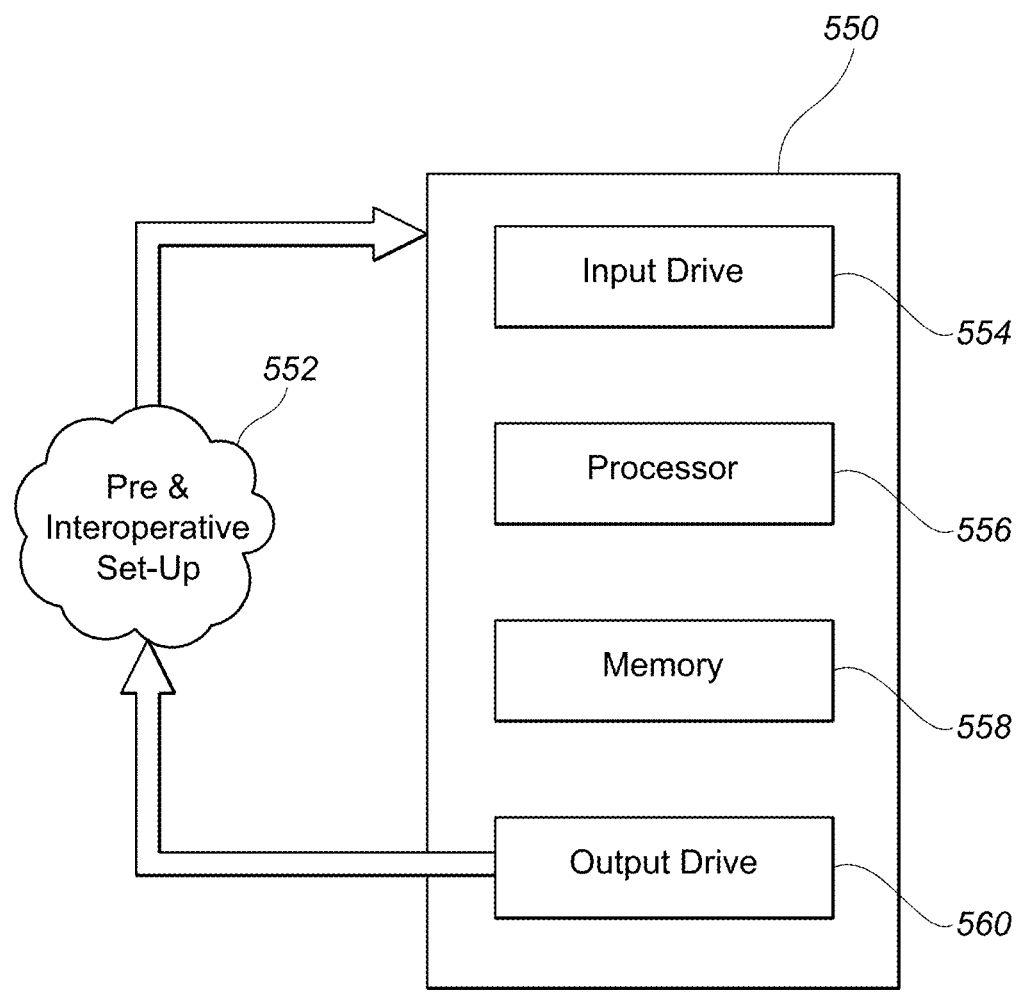
FIG. 18 is a block diagram of the computer overall system architecture of the present invention.

Now referring to FIG. 18 a block diagram of overall system architecture of the present invention is shown in another alternative embodiment. It has a computer-aided system 550 which further includes an input drive 554, a processor 556, a memory 558 and an output drive 560. The computer-aided system 550 assists the surgeon in pre-operative and intra-operative setup 552.

While total hip arthroplasty (THA) is used as an exemplary surgical operation to illustrate in details how the present invention can assist the surgeon in pre-operative planning and intra-operative recommendation. The same system configuration and software modules can be adapted for many other kinds of surgical tasks.

In another embodiment, the digital grid will be applied with same process as hip for trauma fracture reduction and fixation surgery. For example, a tibial plateau fracture or a distal radius wrist fracture. Correct reduction and fixation will be achieved by processing fracture fragments relative to each other and utilizing grid geometry (such as a vertical line for tibial axis line and a 3 degree horizontal line relative to said vertical line) to ensure correct alignment is achieved.

In another embodiment, the appropriate depth of reaming for cup placement during a hip replacement may be quantified relative to anatomical landmarks and the grid. This can allow for visual reference on x-ray image and allow for intra-operative reaming depth boundary and the guidance and placement of the implant relative to this depth stop.

In another embodiment, the appropriate and correct neck cut for stem placement during a hip replacement surgery may be quantified relative to anatomical landmarks and the grid. This can allow for visual reference on x-ray image and allow for correct intraoperative guidance of where to make an accurate neck cut.

In another embodiment the control of anatomical boundaries and acceptable parameters for bone cut limits by utilizing grid as a guide and quantification of said limits allowing forms of RF communication to instruments such as drills or reamers, etc.

In its simplest form, the grid can be digitally displayed over the anatomy and the surgeon can visually determine alignment and positioning measurements.

Clinical Study Example

This retrospective cohort study reviews postoperative radiographic findings of 160 consecutive primary total hip athroplasties performed through an anterior supine approach with the aid of intraoperative fluoroscopy. The control group was 100 total hip athroplasties performed without the grid plate apparatus 19 or 20. The study group was 54 total hip athroplasties performed with the use of the grid plate apparatus 19 or 20 to aid in assessing acetabular component inclination, offset, and leg length. Offset, component abduction and leg length differences were measured by two readers blinded to the group status. Surgeon aims included an inclination angle of 40-45 degrees and a leg length and offset equal to the contralateral side. Additionally, the two groups were assessed for differences in demographics and clinical outcomes including complications such as dislocation and symptomatic leg length discrepancy.

Results:

Inclination angle averaged 42 degrees (SD 1.5 degrees) for the grid group compared to 45 degrees (SD 4 degrees);

Offset averaged +1.5 mm (SD 1 mm) compared to the contralateral side for the grid group compared to −1 mm (SD 3 mm) for the control group;

Leg length differences averaged +1.5 mm (SD 1 mm) compared to the contralateral side for the grid group compared to −1 mm (SD 3 mm) for the control group.

There were no statistically significant differences in age, gender, BMI or dislocation rate between groups. However, the group using the grid plate apparatus 20 had a lower rate of symptomatic leg length discrepancy than the control group.

CONCLUSIONS

While intraoperative use of fluoroscopy to guide offset, leg length and acetabular inclination is helpful, a radiopaque guide with abduction angle references can be helpful to improve precision and accuracy in accomplishing the orthopedic surgeon's goals.

While the invention has been described with reference to preferred and example embodiments, it will be understood by those skilled in the art that a variety of modifications, additions and deletions are within the scope of the invention, as defined by the following claims.

The invention claimed is:

1. A computer implemented system to digitally quantify alignment and placement parameters in a musculoskeletal application comprising:
   a computer system coupled to a radioactive beam emitter and a fluorescent detector, wherein said fluorescent detector is aligned to said radioactive beam emitter to capture an image of a patient;
   said computer implemented system further comprising:
   a microprocessor comprising:
      i. an image capturing module configured to capture an operative image of a portion of said patients body; and
         obtain a reference image of a contra lateral side of said portion of said patient's body;
      ii. a calibration and anatomical matching module coupled to said image capturing module and configured to
         1. calibrate said reference image and said operative image to same magnification;
         2. identify at least one first anatomic marker in said reference image and at least one second corresponding anatomic marker in said operative image; and
         3. produce an overlaid image by overlapping said reference image and said operative image together and anatomically aligning said at least one second anatomic marker against said at least one first anatomic marker on said overlaid image
   a differential mapping module coupled to said calibration and anatomical matching module and configured to digitally quantify alignment and placement parameters in musculoskeletal applications based on said reference image and said operative image taken by said image capturing module, wherein a grid pattern having a radiolucent dimensioned grid plate with a predefined grid pattern and the radiolucent dimensioned grid plate is positioned between the patient and said fluoroscopic detector, and wherein said radiolucent dimensioned grid plate comprises a top surface and a bottom surface, at least one of the top and the bottom surfaces having a plurality of dimensioned radio-opaque horizontal and vertical lines formed thereon; the horizontal and the vertical lines being spaced apart with identical distance between each subsequent vertical line in a horizontal direction and each subsequent horizontal line in a vertical direction; an oblique grid line at an angle of between about 30 to 50 degrees relative to the horizontal lines; and a medial-lateral slot formed in one of the top and bottom surfaces of said grid plate to be parallel to the horizontal lines wherein said computer system further comprises:
   b. the microprocessor coupled to said radioactive beam emitter and said fluorescent detector; and
   c. a non-transitory computer-readable storage medium coupled to said microprocessor, wherein said non-transitory computer-readable storage medium is encoded with computer-readable instructions that implement functionalities of said image capturing module, said calibration and anatomical matching module and said differential matching module wherein said computer-readable instructions are executed by the microprocessor.

2. A computer aided method of adjusting the placement of an implant in a patient, comprising the steps of:
   a. capturing an operative image of a portion of said patient's body where said implant is to be operated on by a fluorescent detector;
   b. obtaining a reference image of a contra lateral side of said portion of said patient's body;
   c. identifying at least one first anatomic marker in said reference image and at least one second corresponding anatomic marker in said operative image;
   d. producing an overlaid image by overlapping said reference image and said operative image together;
   e. anatomically aligning said at least one second anatomic marker against said at least one first anatomic marker on said overlaid image and automatically land marking and segmenting said anatomic markers; and f. determining at least one measurement vital to the operation of said implant based on said overlaid image so that a surgeon can adjust said placement of said implant in said patient based on said at least one measurement, wherein said reference image and said operative image are x-ray images and said identifying step employs one of the following techniques for identifying said anatomic markers
   i. pixel shading and gray contrasting;
   ii. random forest regression;
   iii. hierarchical sparse shape recognition;
   iv. shape detection;
   v. anatomic feature thresholding;
   vi. clustering; or
   vii. any combination thereof;
wherein said measurement quantifies the difference between an anatomic part in said operative image against a corresponding anatomic part in said reference image,
wherein said quantifying step is performed using a grid pattern; and
wherein said grid pattern is a software generated virtual grid that is aligned with said at least one anatomic marker in said operative image; said quantifying step calculating a relative distance between said anatomic part in said operative image and said corresponding anatomic part in said reference image.

3. The method according to claim 2 further comprising the steps of:
   a. providing a radiolucent dimensioned grid plate; said radiolucent dimensioned grid plate comprising said grid pattern;
   b. positioning said radiolucent dimensioned grid plate in between said patient and said fluorescent detector when said reference image and said operative image are being acquired so that a reference grid pattern appears on said reference image and an operative grid pattern appears on said operative image;
   c. calculating at least one displacement between said reference grid pattern and said operative grid pattern;
   d. referencing said anatomic part in said operative image by said operative grid pattern to produce an operative grid coordinate for said anatomic part; and referencing said corresponding anatomic part in said reference image by said reference grid pattern to produce a reference grid coordinate;
   e. subtracting said operative grid coordinate from said reference grid coordinate; and
   f. quantifying said measurement by adjusting the result of said subtraction step with said displacement.

4. The method according to claim 2 wherein said operation is total hip arthroplasty and said at least one measurement vital to said operation is
   a. difference of leg lengths between said operative age and said contra lateral image;
   b. difference of offsets between said operative image and said contra lateral image offset;
   c. difference of hip positions between said operative image and said contra lateral image; or
   d. any combination thereof.

5. The method according to claim 4 further comprising the step of using a hip variance algorithm for recommending surgical procedure.

6. A computer aided method of adjusting a placement of an implant in a patient, comprising the steps of:
   a. capturing an operative image of a portion of said patient's body where said implant is to be operated on by a fluorescent detector;
   b. obtaining a reference image of a contra lateral side of said portion of said patient's body;
   c. identifying at least one first anatomic marker in said reference image and at least one second corresponding anatomic marker in said operative image;
   d. producing an overlaid image by overlapping said reference image and said operative image together;
   e. anatomically aligning said at least one second anatomic marker against said at least one first anatomic marker on said overlaid image and automatically land marking and segmenting said anatomic markers; and
   f. determining at least one measurement vital to the operation of said implant based on said overlaid image so that a surgeon can adjust said placement of said implant in said patient based on said at least one measurement, wherein said reference image and said operative image are x-ray images and said identifying step employs one of the following techniques for identifying said anatomic markers:
      i. pixel shading and gray contrasting;
      ii. random forest regression;
      iii. hierarchical sparse shape recognition;
      iv. shape detection;
      v. anatomic feature thresholding;
      vi. clustering; or
      vii. any combination thereof;
wherein a plurality of specialized pattern recognizers are employed for recognizing said anatomic markers; each of said specialized pattern recognizer being designed for recognizing one anatomic markers; further comprising the step of using a new x-ray image being uploaded into the application to be recognized as a command to display, a pattern included within a preselected sequential set of patterns by said surgeon pre-operatively.

* * * * *